(12) United States Patent
Doron et al.

(10) Patent No.: US 6,239,724 B1
(45) Date of Patent: May 29, 2001

(54) SYSTEM AND METHOD FOR TELEMETRICALLY PROVIDING INTRABODY SPATIAL POSITION

(75) Inventors: Eyal Doron, Kiryat Yam; Yariv Porat, Haifa; Avi Penner, Tel Aviv, all of (IL)

(73) Assignee: Remon Medical Technologies, Ltd., Caesarea (IL)

( * ) Notice: Subject to any disclaimer, the term of this patent is extended or adjusted under 35 U.S.C. 154(b) by 0 days.

(21) Appl. No.: 09/316,397

(22) Filed: May 21, 1999

Related U.S. Application Data

(63) Continuation-in-part of application No. 09/000,553, filed on Dec. 30, 1997, now Pat. No. 6,140,740.

(51) Int. Cl.[7] .................................................. G08C 19/12
(52) U.S. Cl. ............................. 340/870.28; 340/870.07; 340/573.1; 340/10.34; 340/825.99; 128/903; 607/32; 607/60; 600/301
(58) Field of Search ...................... 340/870.28, 825.06, 340/573.1, 870.07, 825.49, 10.1, 10.34; 607/30, 32, 60; 128/903, 904; 600/301, 483, 484, 513

(56) References Cited

U.S. PATENT DOCUMENTS 5,752,976 * 5/1998 Duffin et al. ............................ 607/32
6,083,248 * 7/2000 Thompson .............................. 607/30

* cited by examiner

Primary Examiner—Michael Horabik
Assistant Examiner—Timothy Edward, Jr.

(57) ABSTRACT

A telemetry system and method for providing spatial positioning information from within a patient's body are disclosed. The system includes at least one implantable telemetry unit which includes (a) at least one first transducer being for converting a power signal received from outside the body, into electrical power for powering the at least one implantable telemetry unit; (b) at least one second transducer being for receiving a positioning field signal being received from outside the body; and (c) at least one third transducer being for transmitting a locating signal transmittable outside the body in response to the positioning field signal.

43 Claims, 10 Drawing Sheets

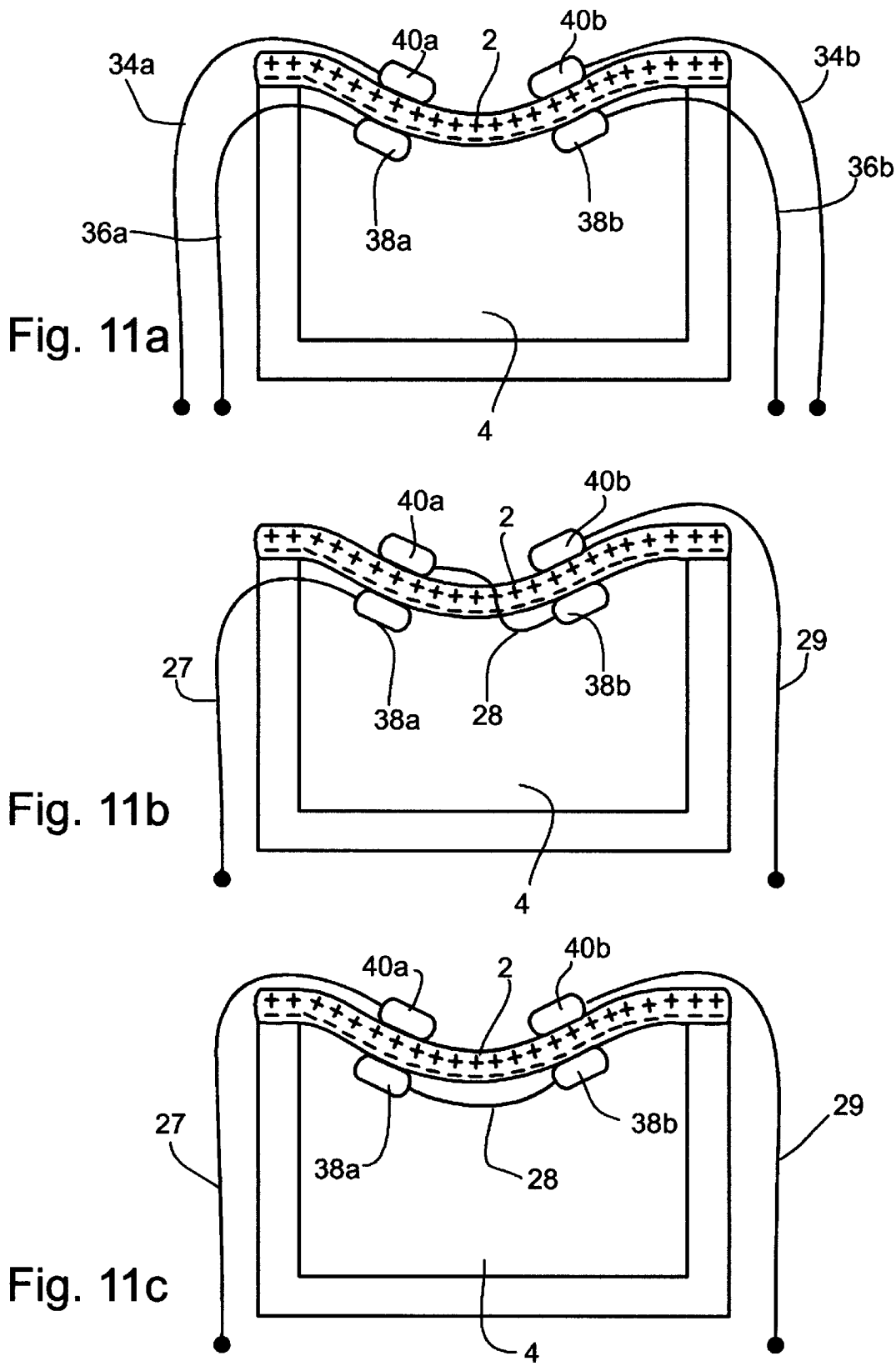

SYSTEM AND METHOD FOR TELEMETRICALLY PROVIDING INTRABODY SPATIAL POSITION

This is a continuation-in-part of U.S. patent application Ser. No. 09/000,553, filed Dec. 30, 1997 now U.S. Pat. No. 6,140,740.

FIELD AND BACKGROUND OF THE INVENTION

The present invention relates to a system and method for positioning a medical instrument and/or directing a medical procedure within a patient's body. More particularly, the present invention relates to an internal power source free transponder, transplantable within the body, which, in response to a positioning field signal, relays a locating signal outside the body, thereby enabling the precise localization of the transponder within the patient's body.

Various medical procedures require precise localization of the three-dimensional position of a specific intra body region in order to effect optimized treatment.

For example, localization and sampling of a suspected tumor is effected in breast biopsy procedures, by typically using a system known as a core biopsy system. The core biopsy system first obtains a stereo-mammogram from a patient's breast, while the breast is immobilized by being compressed between two plates. The stereo-mammogram is used to calculate the three dimensional (3D) coordinates of the suspected tumor. A needle is then fired into the breast and a biopsy of the suspected tumor is aspirated. If the biopsy is positive, the patient is scheduled for a tumor removal surgery. It should be noted that before the biopsy procedure is commenced, the tumor needs to be manually identified by a physician.

Following biopsy of the tumor the surgical procedure, if necessary, generally proceeds in the following manner. The patient undergoes multi-plane mammography, a radiologist examines the film, and then inserts a wire into the breast so that it punctures the tumor. This procedure is visualized using repetitive x-ray imaging or preferably stereotactic breast imaging systems which can localize the tumor more precisely and assist in the insertion of the wire. The surgeon then cuts the breast open, following the wire until the tumor is found and excised.

Although utilizing the core biopsy system along with surgery is currently the method of choice when dealing with breast cancers and various other cancers, such a method suffers from several crucial limitations.

Since there is large difference between the position and shape of the breast during mammography and surgery, images taken during mammography are unusable for stereotactic positioning during the surgical procedure, thus greatly complicating and prolonging the tumor removal procedure and leading to undue discomfort to the patient.

In addition, serious limitations of the above mentioned procedure result from the implantation of a long wire often present in the breast for many hours at a time while the patient awaits surgery. The surgeon must follow this wire into the breast to the located tumor, although ideally, the entry pathway into the breast should be designed independently of the wire, since this implanted wire may not always represent the optimal entrance trajectory. In addition, the presence of wire(s) extending outside the breast greatly increases the risk of infection. Another example of a medical procedure which benefits from tissue region localization is minimally invasive surgery. Although minimally invasive surgery is currently limited in the applications thereof, it presents numerous benefits over conventional surgery. In comparison to conventional surgical methods, minimally invasive surgery reduces the time and trauma of surgery, postoperative pain and recovery time, making the surgical procedure safer and less discomforting to the patient. Examples of medical instruments developed for minimally invasive surgery include laparoscopic, thoracoscopic, endoluminal, perivisceral endoscopic, and intra-articular joint instruments.

Minimally invasive surgery can also use a variety of radiation sources such as lasers, microwaves, and various types of ionizing radiation, to effect tissue manipulation. In addition, cryosurgery has also been used in a minimally invasive manner to treat carcinoma of the prostate, breast, colon and other organs.

A major hurdle facing the surgeon or radiologist in using minimally invasive surgical instruments has been the difficulty in visualizing and positioning such instruments. Decreasing instrument size and increasing complexity of operations have placed greater demands on the surgeon to accurately identify the position of the instruments and the details of the surrounding tissue. Visualization is a critical component to the successful use of minimally invasive surgical or diagnostic instruments.

In laparoscopic surgery, for example, visualization is accomplished by using fiber optics. A bundle of microfilament plastic fibers is incorporated in the instrument and displays a visible image of the field of interest to the surgeon. The quality of this image directly impacts the surgeons ability to successfully manipulate tissue within the patient's body.

Still another area which can benefit from intrabody localization and positioning of tissue regions is robotic assisted surgery. Recent advances in medical imaging technology, such as, for example, magnetic resonance imaging (MRI), especially open-MRI, and computer tomography (CT), coupled with advances in computer-based image processing and modeling capabilities have given physicians the ability to visualize anatomical structures in patient's, in real time, and to use this information in diagnosis and treatment planning.

The precision of image-based pre-surgical planning often greatly exceeds the precision of actual surgical execution. Precise surgical execution has been limited to procedures, such as brain biopsies, in which a suitable stereotactic positioning frame is available. The restricted applicability of such a frame or device has led many researchers to explore the use of robotic devices to augment a surgeon's ability to perform geometrically precise tasks planned from computed tomography (CT) or other available image data. Machines are very precise and untiring and can be equipped with any number of sensory feedback devices. Numerically controlled robots can move a surgical instrument through a defined trajectory with precisely controlled forces. On the other hand, a surgeon is very dexterous, and is highly trained to exploit a variety of tactile and visual information. Although combining the skills of a surgeon with a robotic device can substantially increase the effectiveness and precision of various surgical procedures, such a robotic surgical device must have a precisely defined frame of reference, such as body coordinates, without which it cannot operate with precision.

Yet another type of medical procedure which can greatly benefit from intrabody localization and positioning of tissue regions involves non invasive radiation treatment of tumors, thrombi, vascular occlusions, enlarged prostate, and other physiological disorders.

Examples of such procedures include, but are not limited to, the irradiation of cancerous or benign tumors by a high intensity radioactive source or particle accelerator, the "gamma knife", which employs a highly focused gamma ray radiation obtained from crossing or collimating several gamma radiation beams, the ablation of the prostate by microwave heating, the necrosis of diseased cells following ultrasonic radiation treatment, and local ultrasonically induced drug activation. With all of these applications it is critical that the focus of the energy be precisely directed to the area to be treated, otherwise unwanted damage is inflicted upon the healthy surrounding tissue.

To enable the precise localization of the instruments or radiation beams of the above mentioned procedures, stereotactic positioning is typically employed. This method maps the outer surface of a body, or any part, which is held immobile. Positioning can also employ sensors such as, for example, magnetic sensors (see, for example, U.S. Pat. No. 5,558,091) or acoustic transducers, which are positionably fixed to the skin. In yet another approach, light emitting beacons positioned on the skin, and whose position is measured externally by an appropriate imaging system are used (see, for example, U.S. Pat. No. 5,279,309). The spatial positioning of internal bodily organs is then determined relative to this stereotactic frame using conventional imaging system, such as MRI, CT or ultrasound.

As practiced today, the stereotactic approach is primarily used in intracranial surgical procedures, since the skull provides a convenient and rigid stereotactic frame.

Although using extracorporeal referencing devices and methods is advantageous for being non invasive, such positioning means are limited by the fact that the position of intrabody regions of interest constantly change, either due to deformation of elastic structures (e.g., the breast, organs inside the abdominal cavity) or due to the progression of the disease (e.g., intracranial swelling). Thus, stereotactic methods cannot be used for precise and automated medical procedures, especially those relating to soft tissue.

An alternative procedure is disclosed in U.S. Pat. No. 5,868,673 which describes a spatial tracking and imaging system for obtaining an accurate position of a medical instrument as it is maneuvered by an operator, and to mark a location on the subject bodily structure. The spatial positioning is effected by implanting reference transducers at the desired location in the body, which are connected by thin wires to connection pads or electronic circuits placed externally to the body. The transducers can receive and/or transmit ultrasonic energy, and as such signal their position relative to a set of mobile transducers placed at known locations on the body at the time of the procedure. The mobile and reference transducers communicate by sending ultrasonic impulses in either direction, which yields the relative position of the reference transducers. Alternatively, the mobile transducer may be placed at the tip of a surgical device, and as such employed to guide the tip in relation to the reference transducers.

This system suffers from several limitations resultant from the extracorporeal wire connection of the implanted reference transducer. The use of such wires prevents the use of this design in intracranial applications, such as, for example, intracranial surgery. Further still, externally provided wires traversing the body into deep internal organs serve as potential conduits for infection. A further limitation of this design is that wired devices cannot be left inside the body, but instead, have to be removed within a relatively short time following the procedure. The removal procedure, which may necessitate full surgery, can be more traumatic to the patient than the insertion. In addition, since discomfort to the patient is wantedly minimized, such wires have to be thin, and as such fragile, and can break during the surgical procedure. Such a sudden loss of positioning information in the course of a surgical procedure can lead to catastrophic results.

In addition to the limitations imposed by the wiring of the reference transducer, a further disadvantage of the above mentioned method is that it yields only positions relative to external reference points provided by the reference transducers which are placed in contact with the patient's skin. In applications which involve radiation that emerges from fixed sources (e.g., the collimated gamma radiation beams used in a "gamma knife"), it would be advantageous to have spatial positioning information relative to the radiation source. Such information cannot be provided by the system disclosed in U.S. Pat. No. 5,868,673.

Finally, the above mentioned system depends on the transmission of acoustic signals to obtain the positioning information, using either time-of-flight or phase information. Such a system is rendered unusable in some surgical procedures. During surgery various air gaps are opened in the body, caused by small openings opened in minimally invasive procedures, inflating the abdominal cavity with carbon dioxide during some laparoscopic procedures, or full open surgery. Such air gaps either cut off ultrasonic communication between the reference and mobile transducers, or change the intra-body acoustic propagation conditions so that precise positioning information is hard to obtain.

Another position localization approach comprises the implantation of fiducial markers at various positions within the body (see, for example, U.S. Pat. Nos. 4,945,914; 4,991,579; 5,394,457; and 5,397,329). In these systems and methods, the implants comprise a passive structure which is limited in properties to a specific imaging system. Typically, and as disclosed in the above referenced patents, fiducial markers include contrast materials for MRI, X-ray fluoroscopy or CT scanners and ultrasound. The imaging data is scanned for the presence and position of such markers, and these positions, when processed through a dedicated algorithm, form the anchor points for the spatial positioning reference frame.

Systems and methods incorporating fiducial markers are advantageous in being standalone implantable devices, which do not require external connections. However, each marker type can only be used with a specific imaging system, which greatly limits the application of such markers. In addition, when utilizing X-ray fluoroscopy or CT markers, the imaging process necessitates exposure to ionizing radiation. Furthermore, MRI and CT systems are bulky, intrusive and complicated to operate. Finally, ultrasonic imaging systems, for the most part, do not yield independent 3D positions, and suffer from the disadvantages detailed above.

Yet another positioning method is disclosed in U.S. Pat. No. 5,161,536 which describes the implantation of an actual active transponder inside the body. This transponder actively returns ultrasonic pulses sent by a probe of a conventional ultrasonic imaging system. The returning pulse is picked up, synchronized and analyzed by the imaging system to yield the position of the implant superimposed on the ultrasound image. This ensures a good signal-to-noise ratio, ease of operation, and also avoids the ambiguities associated with transmission sidelobes. However, it does share most of the disadvantages of other fiducial marker methods. In addition, it requires an independent power source, such as a battery, which limits its lifespan and increases the size of such a transponder.

Thus, a limitation common to all of the above mentioned positioning systems and methods is the lack of precise, telemetric, spatial localization of intrabody regions provided as information which is usable as machine input.

There is thus a widely recognized need for, and it would be highly advantageous to have, a system and method for positioning a medical instrument and/or directing a medical procedure within a patient's body devoid of the above limitation.

SUMMARY OF THE INVENTION

According to one aspect of the present invention there is provided a telemetry system for providing spatial positioning information from within a patient's body, the system comprising at least one implantable telemetry unit including (a) at least one first transducer being for converting a power signal received from outside the body, into electrical power for powering the at least one implantable telemetry unit; (b) at least one second transducer being for receiving a positioning field signal being received from outside the body; and (c) at least one third transducer being for transmitting a locating signal transmittable outside the body in response to the positioning field signal.

According to another aspect of the present invention there is provided a method for obtaining spatial positioning information from within a patient's body, the method comprising the steps of (a) implanting within the patient's body at least one telemetry unit including (i) at least one first transducer being for converting a power signal received from outside the body, into electrical power for powering the at least one implantable telemetry unit; (ii) at least one second transducer being for receiving a positioning field signal being received from outside the body; and (iii) at least one third transducer being for transmitting a locating signal transmittable outside the body in response to the positioning field signal; and (b) receiving the locating signal outside the body of the patient, such that the location of the at least one telemetry unit within the body of the patient is identified from the locating signal.

According to further features in preferred embodiments of the invention described below, the spatial positioning information is used to direct radiation to a specific region within the patient's body.

According to still further features in the described preferred embodiments the radiation is selected from the group consisting of ultrasonic radiation and ionizing radiation.

According to still further features in the described preferred embodiments the ionizing radiation is selected from the group consisting of alpha radiation, beta radiation, gamma radiation, X-ray radiation and neutron radiation.

According to still further features in the described preferred embodiments the power signal is selected from the group consisting of a to radio frequency signal, an acoustic signal and a magnetic field signal.

According to still further features in the described preferred embodiments the positioning field signal is selected from the group consisting of a radio frequency signal, an acoustic signal and a magnetic field signal.

According to still further features in the described preferred embodiments the at least one first and the at least one third transducers are each independently selected from the group consisting of a radio frequency transducer, an acoustic transducer and a magnetic field transducer.

According to still further features in the described preferred embodiments the at least one first transducer and the at least one third transducer are a single transducer.

According to still further features in the described preferred embodiments the single transducer is selected from the group consisting of radio frequency transducer, an acoustic transducer and a magnetic field transducer.

According to still further features in the described preferred embodiments the method further comprising the step of processing a first electrical signal converted by the at least one second transducer from the positioning field signal and returning a processed second electrical signal to the at least one third transducer via a processor being within the at least one telemetry unit, such that the second electrical signal is converted into the locating signal by the at least one third transducer.

According to still further features in the described preferred embodiments the at least one first transducer and the at least one third transducer are each independently an acoustic transducer which-includes (i) a cell member having a cavity; (ii) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (iii) a first electrode attached to the external surface and a second electrode attached to the internal surface.

According to still further features in the described preferred embodiments the piezoelectric layer is of a material selected from the group consisting of PVDF and piezoceramic.

According to still further features in the described preferred embodiments the magnetic field transducer of the at least one first transducer includes at least one coil for converting a magnetic field signal into an electrical current.

According to still further features in the described preferred embodiments the magnetic field transducer of the at least one second transducer is selected from the group consisting of multiturn wire coils, coils implemented in a very large scale integration (VLSI) silicon devices, a Hall effect detector, a coupled split-drain field effect transistor (MAGFET) device, and a magnetoresistive field effect transistor (FET) detector.

According to still further features in the described preferred embodiments the magnetic field transducer of the at least one second transducer includes a plurality of transducers each for converting a magnetic field signal into an electrical signal.

According to still further features in the described preferred embodiments the plurality of transducers are oriented in three mutually orthogonal planes.

According to still further features in the described preferred embodiments the step of receiving the locating signal outside the body of the patient is further effected by an extracorporeal monitoring unit telemetrically communicating with the at least one telemetry unit.

According to still further features in the described preferred embodiments the step of telemetrically communicating i s achieved via a signal selected from the group consisting of an acoustic signal, a magnetic signal and a radio frequency signal.

According to still further features in the described preferred embodiments each of the at least one telemetry unit has an identification code associated therewith.

According to still further features in the described preferred embodiments information pertaining to the identification code is included within the locating signal.

According to still further features in the described preferred embodiments the at least one telemetry unit is implanted in a specific predefined region of the patient's body and further wherein the identification code includes predefined spatial positioning information.

The present invention successfully addresses the shortcomings of the presently known configurations by providing a system and method for positioning a medical instrument and/or directing a medical procedure within a patient's body devoid of the limitations associated with prior art systems and which can provide an integrated system operating to provide positional information of a medical instrument in a most efficient manner.

BRIEF DESCRIPTION OF THE DRAWINGS

The invention herein described, by way of example only, with reference to the accompanying drawings, wherein:

FIG. 6a is a cross section of a transducer element according to the present invention taken along line C—C in FIG. 5a;

FIG. 6b is a cross section of a transducer element according to the present invention taken along line D—D in FIG. 5a;

FIG. 6c is a cross section of a transducer element according to the present invention taken along line E—E in FIG. 5a;

FIG. 6d is a cross section of a transducer element according to the present invention taken along line F—F in FIG. 5a;

FIG. 6e is a cross section of a transducer element according to the present invention taken along line G—G in FIG. 5a;

FIGS. 11a–11f are schematic views of possible configurations of transmitters according to the present invention including parallel and anti-parallel electrical connections for controllably changing the mechanical impedance of the piezoelectric layer;

DESCRIPTION OF THE PREFFERRED EMBODIMENTS

Figure 1:
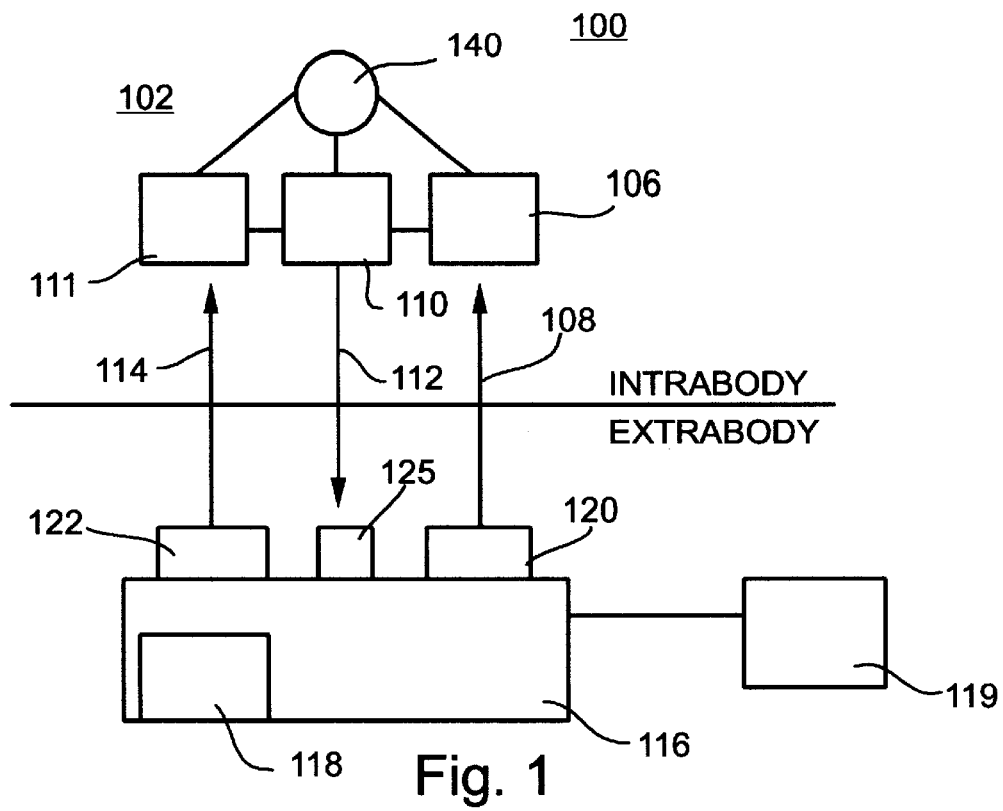
FIG. 1 is a schematic depiction of a telemetry system for providing spatial positioning information from within a patient's body according to one embodiment of the present invention.

The present invention is of a system and method which can be used to position a medical instrument and/or to direct a medical procedure within a patient's body. Specifically, the present invention can be used to provide, outside the patient's body, information pertaining to the spatial positioning of implantable telemetry devices, such that a medical instrument and/or a medical procedure can be directed within the patient's body according to this information.

The principles and operation of a according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1–4 illustrate the telemetry system according to the present invention, which is referred to hereinbelow as system 100.

System 100 serves for providing spatial positioning information from within a patient's body. Thus, as further described hereinunder, system 100 can be used to accurately direct a medical instrument, such as, but not limited to, a non-invasive medical instrument, e.g., a medical radiation source, or an invasive or minimally invasive medical instrument, e.g., a drill, an endoscope, a laparoscope or a biopsy needle, and/or a medical procedure, such as, but not limited to, a therapeutic radiation treatment, to thereby improve the precision and thus effectiveness while using such medical instruments and/or implementing such procedures.

As shown in FIG. 1, system 100 includes at least one intrabodily implantable telemetry unit 102. Implantable telemetry unit 102 includes a first transducer 106 which serves for converting a power signal (as indicated by 108) received from outside the body, into electrical power for powering implantable telemetry unit 102.

Implantable telemetry telemetry unit 102 further includes a second transducer 111 which serves to receive a positioning field signal 114 which is transmitted from outside the body.

Implantable telemetry unit 102 further includes a third transducer 110 which serves for transmitting a locating signal (as indicated by 112) which is transmitted outside the body of the patient in response to a positioning field signal (as indicated by 114).

Thus, according to one aspect of the present invention, in order to provide spatial positioning information from within a patient's body, at least one, preferably a plurality of implantable telemetry units 102 are implanted within a region of the patient's body. Preferably, telemetry unit(s) 102 are implanted within, and/or in close proximity to, the region to be treated. Power signal 108 receivable by telemetry unit(s) 102 is generated by, and transmitted from, an extracorporeal unit 116, the construction and operation of which is further detailed hereinbelow. Concomitantly with, or shortly after, the generation of power signal 108, positioning field signal 114 is generated and transmitted from extracorporeal unit 116. Positioning field signal 114 is received by telemetry unit 102 which produces in response thereto locating signal 112, which is transmitted from telemetry unit 102 outside the body of the patient. Locating signal 112 is received and analyzed by extracorporeal unit 116. As a result, information pertaining to the spatial position of each of the plurality of implantable telemetry unit(s) 102 is recorded.

As further described hereinunder this positioning information creates reference points with which a medical instrument or a medical procedure can be consequently navigated.

Figure 4:
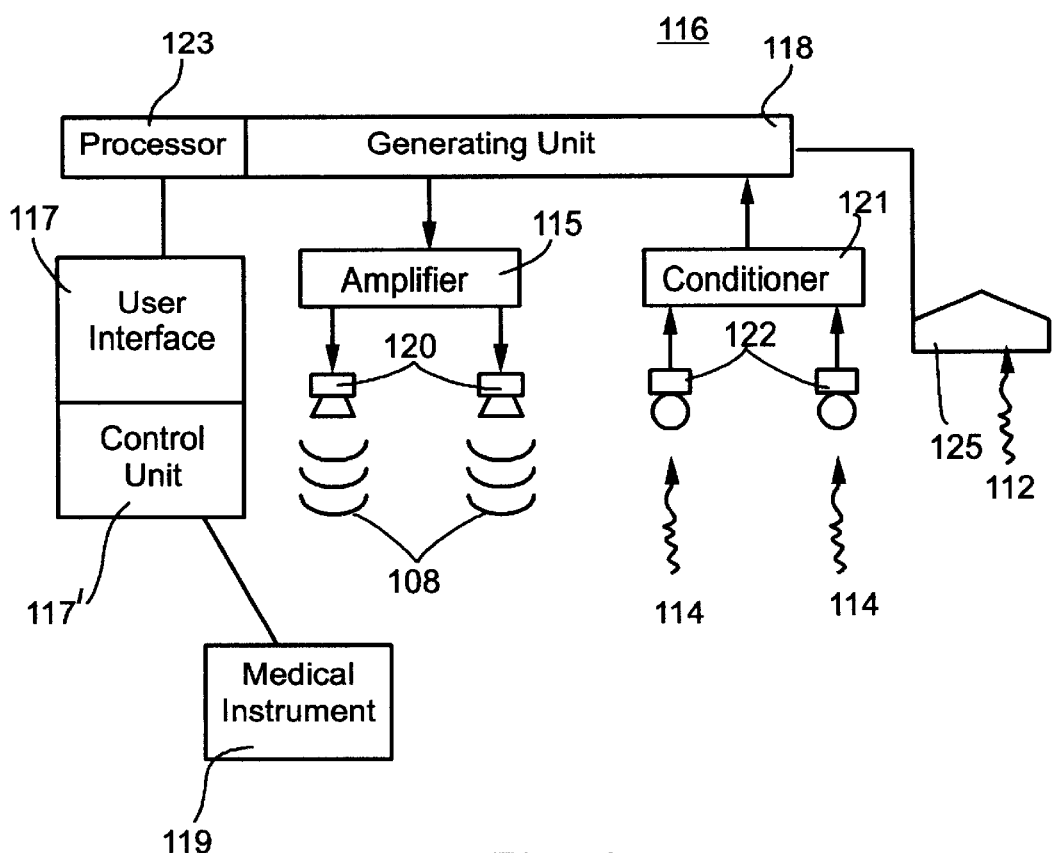
FIG. 4 is a block diagram of an extracorporeal unit of the system according to the present invention.

Extracorporeal unit 116 is shown in more detail in FIG. 4. Extracorporeal unit 116 includes a generating unit 118. Unit 118 serves for generating power signal 108. Unit 118 preferably also serves for generating positioning field signal 114. As further detailed hereinunder, unit 118 assists in receiving locating signal 112. Extracorporeal unit 116 also includes a fourth transducer 120 which is coupled to generating unit 118. Transducer 120 serves for transmitting power signal 108, which is generated by unit 118 and which is amplified via an amplifier 115, to implantable telemetry unit 102. In addition, extracorporeal unit 116 also includes a fifth transducer 122 which is coupled to generating unit 118. Transducer 122 serves for transmitting positioning field signal 114 which is receivable by implantable telemetry unit 102. In addition, extracorporeal unit 116 also includes a sixth transducer 125 which is coupled to generating unit 118. Transducer 125 serves for receiving locating signal 112 from implantable telemetry unit 102.

Signal 112 is conditioned via a conditioner 121 and is delivered to a user interface 117 via generating unit 118. To this end, generating unit 118 also includes a processor 123 which serves for processing signal 112. Extracorporeal unit 116 also includes a control unit 117' which together with interface 117 serves for displaying and controlling spatial positioning information extracted from signal 112. User interface 117 and control unit 117' also serve for directing a medical instrument 119, either invasive, minimally invasive or non-invasive instrument, with respect to, or within, the patient's body.

As already mentioned hereinabove, telemetry unit 102 includes transducers 106, 110 and 111 which serve for communicating with extracorporeal unit 116.

According to one preferred embodiment of the present invention transducers 110 and 106 are radio frequency transducers designed to receive and transmit signals within the radio frequency range. Since radio frequency signals do not propagate well within body tissues, but, on the other hand, propagate well within air or gas, an implantable telemetry unit 102 incorporating radio frequency transducers is preferably implanted in the body of a patient undergoing open surgical procedures such as, for example, laparoscopic procedures, or full open surgery. In such procedures large air gaps are opened within the body of the patient. Such air gaps enable the efficient propagation of radio frequency signals.

According to a preferred embodiment of the present invention radio frequency transducer 110 employs Lumped-Constant (L-C) circuits. Transducers incorporating L-C circuits are well known in the art and therefore require no further description herein. For example, U.S. Pat. Nos. 3,943,915 and 4,593,703, which are incorporated herein by reference, teach transducers incorporating L-C circuits which are employed to relay information from an implantable intracranial pressure sensor outside the body of the patient.

According to another preferred embodiment of the present invention, transducers 106 and 110 of telemetry unit 102 are acoustic transducers. In cases where the implantation of telemetry unit 102 is utilized to provide spatial positioning information for non-invasive procedures such as a radiation treatment, acoustic transducers are particularly advantageous since acoustic signals are readily transmittable with relatively small losses through water-bearing bodies such as bodies of living creatures.

The operation of acoustic transducers which are suitable for the above mentioned use is described in detail in U.S. patent application Ser. No. 09/000,553, which is incorporated herein by reference and further in the Example section that follows.

According to another preferred embodiment of the present invention transducers 106 and 110 are magnetic field transducers, for example, multiturn wire coils, or coils implemented in VLSI (very large scale integrated silicon devices).

Telemetry system 102 which includes magnetic field transducers can be utilized in a variety of procedures, ranging from full open surgical to non-invasive procedures.

As already mentioned hereinabove, telemetry unit 102 includes transducer 111 which serve for receiving positioning field signal 114 generated by extracorporeal unit 116.

According to a preferred embodiment of the present invention transducer 111 includes one or more magnetic field transducers. Such magnetic field transducers can include, for example, multiturn wire coils, coils implemented in VLSI (very large scale integration) devices, Hall effect detectors (see, for example, U.S. Pat. No. 5,528,067, which is incorporated herein by reference), coupled MAG-FET (split-drain field effect transistors, see, for example, U.S. Pat. No. 5,438,990, which is incorporated herein by reference) devices or magnetoresistive FET (field effect transistor) detectors.

Preferably, transducer 111 uses at least three mutually orthogonal multiturn wire coils or any of the similar functioning elements mentioned above, thus enabling transducer 111 to measure both the magnitude and the orientation of the externally generated magnetic positioning field signal.

A telemetry system 102 which includes magnetic field transducers can be utilized in a variety of procedures, ranging from full open surgical to non-invasive procedures. Magnetic field transducers which yield positioning information are well known in the art. For further detail, see, for example, U.S. Pat. Nos. 4,845,503; 5,729,129 and 5,558,091, which are incorporated herein by reference.

Alternatively and according to another preferred embodiment of the present invention transducer 111 is an acoustic transducer. Acoustic transducers are known in the art, see, for example U.S. Pat. No. 4,697,595, which is incorporated herein by reference. Preferably acoustic transducer 111 is a piezoelectric ultrasound receiver, many types and configurations of which are well known in the art.

According to this embodiment, positioning field signal 114 is an acoustic signal which when received by acoustic transducer 111 enables the positioning of telemetry unit 102 as further described hereinabove.

It will be appreciated by one ordinarily skilled in the art that transducers 106,–110 and 111 of telemetry unit 102 can each independently be selected from any of the transducers mentioned above. As such, a combination of the above transducers, such as, for example, acoustic transducers 106 and 110 and magnetic field transducer 111 can be constructed and utilized by the system of the present invention. It will further be appreciated that such combinations, when incorporated into telemetry unit 102, can be particularly advantageous in customizing telemetry unit 102 to most efficiently function with a specific medical instrument and/or procedure.

Figure 2:
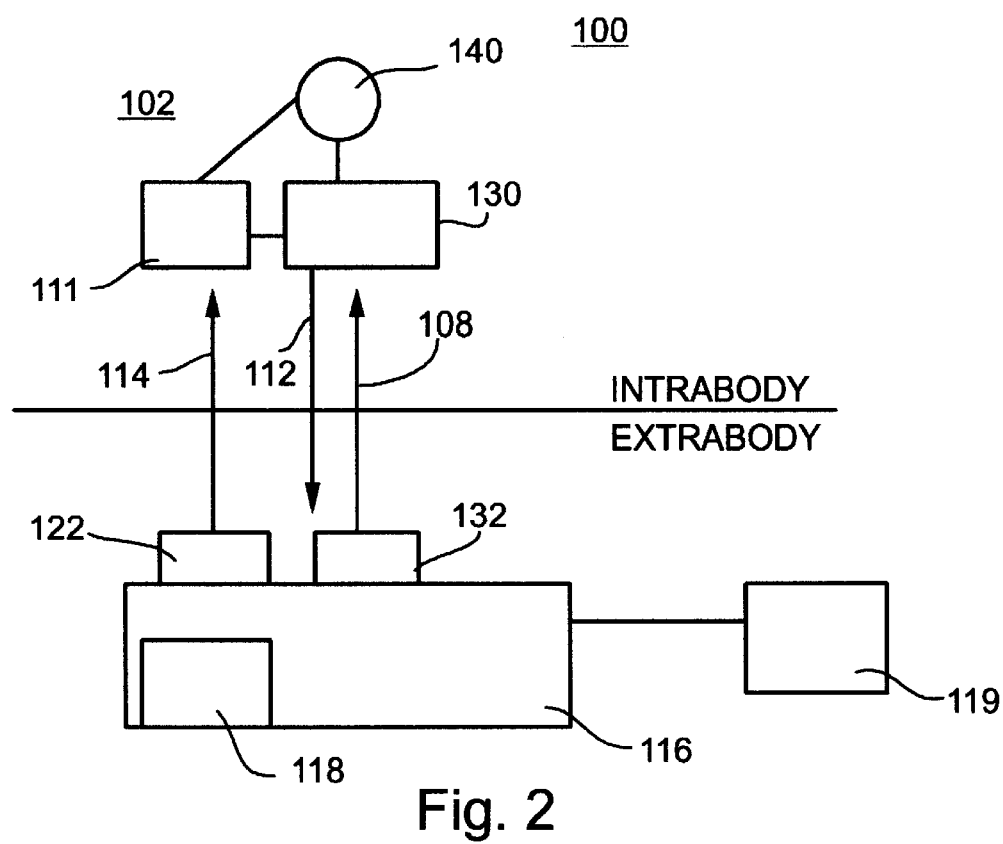
FIG. 2 is a schematic depiction of a telemetry system for providing spatial positioning information from within a patient's body according to another embodiment of the present invention.

According to another preferred embodiment of the present invention, and as specifically shown in FIG. 2, the function of transducers 106 and 110 is integrated into a single transducer 130. In addition, the function transducers 120 and 125 of extracorporeal unit 116 can also be integrated into a single transducer 132.

According to another preferred embodiment of the present invention, telemetry unit 102 also includes a processor 140. As shown in FIG. 1, processor 140 communicates with transducers 106, 110 and 111, or alternatively, as shown in FIG. 2, with transducers 130 and 111. Processor 140 serves for conditioning positioning field signal 114 and for multiplexing and modulating the transmitted locating signal 112.

Figure 3:
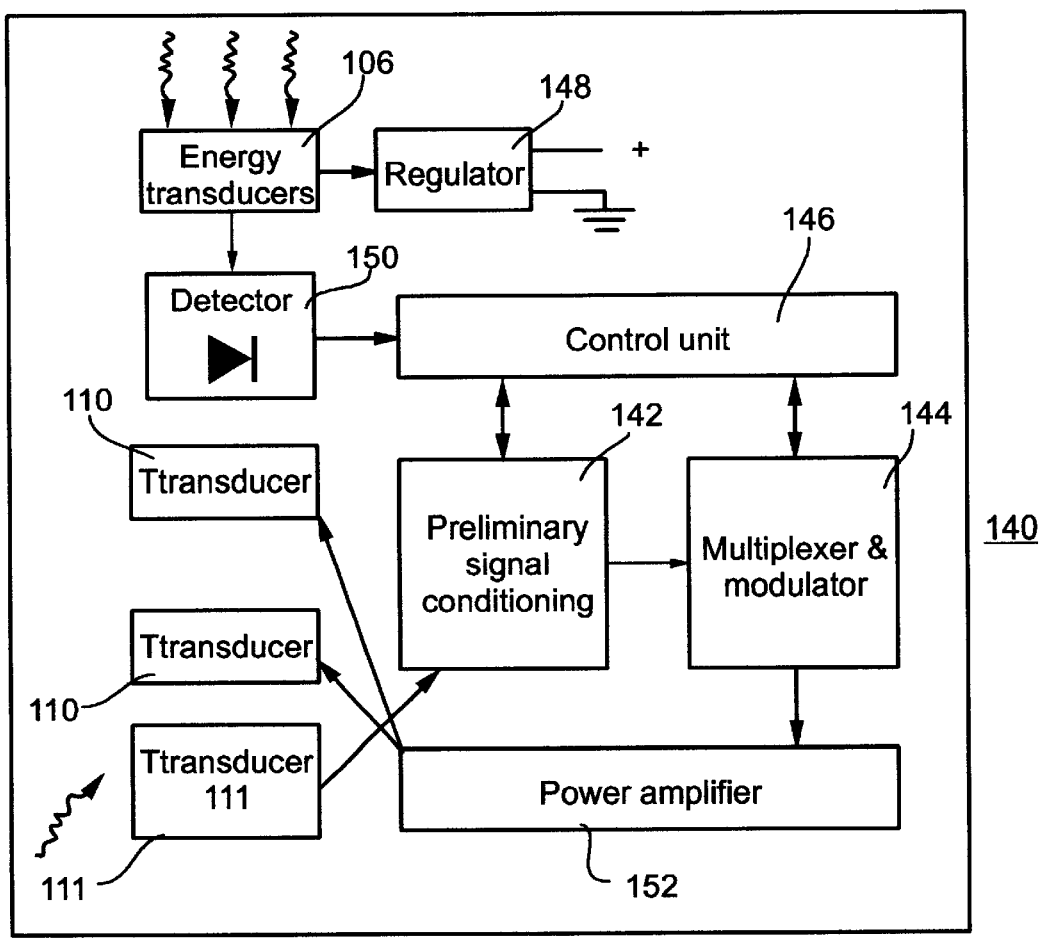
FIG. 3 is a block diagram of an implantable telemetry unit of the system according to the present invention.

To this end, and as specifically shown in FIG. 3, processor 140 includes a conditioner 142, a multiplexer and modulator 144, both communicating with a control unit 146. Control unit 146 receives an electrical signal which was converted from power signal 108 by transducer 106. Preferably the electrical signal received by unit 146 is converted into a direct current signal via a regulator 148.

In addition, in order to be able to recognize and differentially power a specific telemetry unit 102 when a plurality of units 102 are utilized by system 100, each telemetry unit 102 is coded with an activation code, so as to allow utilization of a specific unit 102 as desired. In addition, unit 102 can be encoded with a location code so as to allow spatial positioning out of the body of the patient.

For example, an activation code can be associated with each telemetry unit 102, such that a specific activation code carried preferably within power signal 108 is recognized by a detector 150 and as such allows powering and thus functioning of a specific telemetry unit 102.

In addition, each telemetry unit 102 can also optionally include a location code associated with processor 140, such that when a locating signal is generated it includes a location code within the locating signal transmitted. In this case, processor 140 of telemetry unit 102 can be programmed prior to implantation with a code specific to the region in which unit 102 is to be implanted, such that when this code is transmitted along with the locating signal the location of unit 102 is identified.

As such, when unit 102 is powered and receives via transducer 111 positioning signal 114, locating signal 112 is generated from processor 140, amplified via power amplifier 152 and returned to transducers 110 to be transmitted outside the patient's body.

To yield spatial positional information, the information carried within locating signal 112 generated from each telemetry unit 102 can be analyzed by extracorporeal unit 116 in a manner suitable to the positioning strategy being used.

For the case of an acoustic positioning field signal 114 and acoustic transducers 111 and 122, this can be achieved by calculating the time of flight for each signal and thus calculating the distance of the implanted unit 102 from extracorporeal unit 116. In this case, a minimum of three positioning field signal transmitters 122 are required to effect localization.

For the case of a magnetic positioning field signal 114 and magnetic transducers 111 and 122, this can be achieved by comparing the orientation of one or more externally generated magnetic fields to a previously tabulated volumetric map. In this case, incorporating additional extracorporeal transducers 122 with which both the position and the orientation of telemetry unit 102 can be obtained is preferred The above methods can be used to create spatial position reference points so as to enable medical instrument 119 which is communicating with extracorporeal unit 116 to be directed according to these points to a specific region of a patient's body.

It will be appreciated that positioning algorithms which can be utilized by the system of the present invention to provide the relative position of the medical instrument in reference to the spatial position of telemetry unit 102 are well known in the art and thus require no further explanation herein.

Directing instrument 119 according to the present invention can be effected manually in accordance to information communicated to a user via interface 117. Alternatively, and presently preferably, medical instrument 119 is automatically directed in reference to spatial positions generated by implanted telemetry unit(s) 102 to provide treatment to a preselected region of the patient's body. In the latter case, a user can optionally program, via user interface 117, a specific event executable by medical instrument 119.

Basically, system 100 according to the present invention provides a set of spatial reference points from within the patient's body, which are equivalent, in this respect, to fiducial markers. However, an inherent advantage of the present invention as compared to fiducial markers lies in its ability to return precise and absolute positioning information with respect to a rigid external frame of reference, autonomously and without the need to incorporate an additional, possibly intrusive and/or cumbersome imaging and tracking system. An additional advantage of the present invention, as compared to fiducial markers, is its universality. In other words, while fiducial markers are selected compatible to the imaging method employed for their recognition within the body, such as ultrasound or fluoroscopy, and as such positioning data derived therefrom should be introduced into a second positioning system which is employed for positioning a surgical instrument, the system according to the present invention operates according to preferred embodiments both with the intrabody implantable telemetry unit and with an equivalent telemetry unit integrated in the medical instrument. Thus, a single extracorporeal unit retrieves stationary positional information from the implantable telemetry units and further retrieves trackable positional information from the telemetry unit integrated in the medical instrument, to thereby provide tracking thereof relative to the implantable telemetry units. In sharp contrast, when employing fiducial markers, in many cases, two independent and totally different extracorporeal stations are employed, whereas positional information is communicated following the appropriate processing therebetween.

In a most preferred embodiment, the extracorporeal unit of the system according to the present invention is integrated into the medical instrument, such that the relation thereof with respect to the implantable telemetry units is directly obtained. Thus, when the term "extracorporeal unit" is used herein, it also refers to situations wherein such a unit or components thereof are transiently introduced into the body along with a medical instrument onto or into which it is integrated.

Not withstanding from the above, the system according to the present invention can also be operated in a fashion similar to fiducial markers based systems. In this case, both an extracorporeal unit as herein described and an independent, typically different, extracorporeal station which serves for tracking the medical instrument are to communicate positional data therebetween.

For system 100 to function properly and efficiently, implanted telemetry unit 102, which can include acoustic, radio frequency, or magnetic field powering transducer(s), must be miniature in size and produce from the impinging signal the power necessary for the various functions thereof.

The electronic circuitry can be built around existing ultra-low-power microprocessing cores. For example, one can use the XE8851 microcontroller with integrated analog-to-digital converter supplied by Xemics SA of Neuchatel, Switzerland. This processor core uses RISC technology, contains integrated ROM and RAM memory, operates on 1.2 V and consumes less than 200 $\mu$A at 1 MHz clock rate, down to less than 30 $\mu$A at 32 kHz clock rate. The area of such a processor is a few mm$^2$.

The current consumed by the magnetic field sensors depends on their structure. Magnetic pickup coils do not require any current to operate, rather they produce current in response to a magnetic field signal. The only power requirement comes from the amplifiers. Using FET input stages, a power requirement of an amplification stage can be 5 $\mu$W or less. MAGFET and Hall effect sensors also require extremely low power in order to operate, due to the high input impedances of FET devices.

Another power consumer is the receiving/transmitting capable transducer (which is represented by transducer 110 above) which transmits locating signal 112. Such a transducer is an efficient data transmitter, which to reach the desired acoustic power requirements of a few $\mu$W requires no more than 10–20 $\mu$W of electrical power even in a very inefficient system.

The above power requirements can be easily satisfied by, for example, acoustic transducers. A single transducer cell, of the type described in the Example section that follows, has a diameter of around 1 mm and thickness of roughly 0.15 mm. Such a cell can be made to yield 100–200 $\mu$W of electrical energy for a surface area of 0.8 mm$^2$.

Thus, in order to supply the energy requirements of telemetry unit 102 and in order to provide telemetry unit 102 with a wide application range, a preferable configuration of telemetry unit 102 includes an acoustic transducer 106 for powering unit 102, acoustic transducer 110 for transmitting the locating signal out of the body, and magnetic field transducer 111 for communicating with magnetic field transducer 122 of extracorporeal unit 116.

As such, sufficient power to energize system 100 can be acquired from a few acoustic transducers. To this end, a possible device configuration could be for example, a cylindrical structure, 2–3 mm in diameter and 3–5 mm in length. Such a structure can easily include both the electronics, the powering acoustic transducers, and the transcieving magnetic field transducers. Such a device is small enough to be implantable in a minimally invasive manner via a standard biopsy needle.

The spatial positioning system of the present invention provides a precise and simple means to generate position reference points which can be used as information to direct a medical instrument.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

For purposes of better understanding the construction and operation of an acoustic transducer utilizable by the system of the present invention, reference is made to the construction and operation of an acoustic transducer as described in U.S. patent application Ser. No. 09/000,553.

Referring again to the drawings, FIGS. 5a, 5b and 6a–6e illustrate a preferred embodiment of a transducer element according to the present invention. As shown in the Figures, a transducer element 1 includes at least one cell member 3 including a cavity 4 etched into a substrate and covered by a substantially flexible piezoelectric layer 2. Attached to piezoelectric layer 2 are an upper electrode 8 and a lower electrode 6, the electrodes for connection to an electronic circuit.

The substrate is preferably made of an electrical conducting layer 11 disposed on an electrically insulating layer 12, such that cavity 4 is etched substantially through the thickness of electrically conducting layer 11.

Electrically conducting layer 11 is preferably made of copper and insulating layer 12 is preferably made of a polymer such as polyimide. Conventional copper-plated polymer laminate such as KAPTON™ sheets may be used for the production of transducer element 1. Commercially available laminates such as NOVACLAD™ may be used. Alternatively, the substrate may include a silicon layer, or any other suitable material. Alternatively, layer 11 is made of a non-conductive material such as PYRALIN™.

Preferably, cavity 4 is etched into the substrate by using conventional printed-circuit photolithography methods. Alternatively, cavity 4 may be etched into the substrate by using VLSI/micro-machining technology or any other suitable technology.

Piezoelectric layer 2 may be made of PVDF or a copolymer thereof. Alternatively, piezoelectric layer 2 is made of a substantially flexible piezoceramic. Preferably, piezoelectric layer 2 is a poled PVDF sheet having a thickness of about 9–28 $\mu$m. Preferably, the thickness and radius of flexible layer 2, as well as the pressure within cavity 4, are specifically selected so as to provide a predetermined resonant frequency. When using the embodiment of FIGS. 5a and 5b, the radius of layer 2 is defined by the radius of cavity 4.

By using a substantially flexible piezoelectric layer 2, the invention described in U.S. patent application Ser. No. 09/000,553 allows to provide a miniature transducer element whose resonant frequency is such that the acoustic wavelength is much larger than the extent of the transducer. This enables the transducer to be omnidirectional even at resonance, and further allows the use of relatively low frequency acoustic signals which do not suffer from significant attenuation in the surrounding medium.

Prior art designs of miniature transducers, however, rely on rigid piezoceramic usually operating in thickness mode. In such cases the resonant frequency relates to the size of the element and speed of sound in the piezoceramic, and is higher by several orders of magnitude.

The invention described in U.S. patent application Ser. No. 09/000,553 provides a transducer which is omnidirectional, i.e., insensitive to the direction of the impinging acoustic rays, thereby substantially simplifying the transducer's operation relative to other resonant devices. Such a transducer element is thus suitable for application in confined or hidden locations, where the orientation of the transducer element cannot be ascertained in advance.

According to a specific embodiment, cavity 4 features a circular or hexagonal shape with radius of about 200 $\mu$m. Electrically conducting layer 11 preferably has a thickness of about 15 $\mu$m. Cell member 3 is preferably etched completely through the thickness of electrically conducting layer 11. Electrically insulating layer 12 preferably features a thickness of about 50 $\mu$m. The precise dimensions of the various elements of a transducer element according to the invention described in U.S. patent application Ser. No. 09/000,553 may be specifically tailored according to the requirements of the specific application.

Cavity 4 preferably includes a gas such as air. The pressure of gas within cavity 4 may be specifically selected so as to predetermine the sensitivity and ruggedness of the transducer as well as the resonant frequency of layer 2.

Figure 6A:
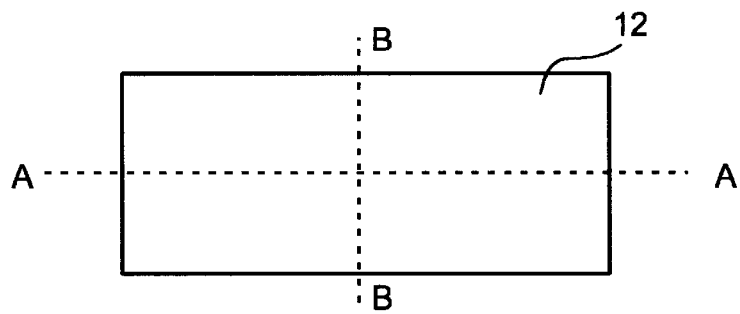
Figure 6B:
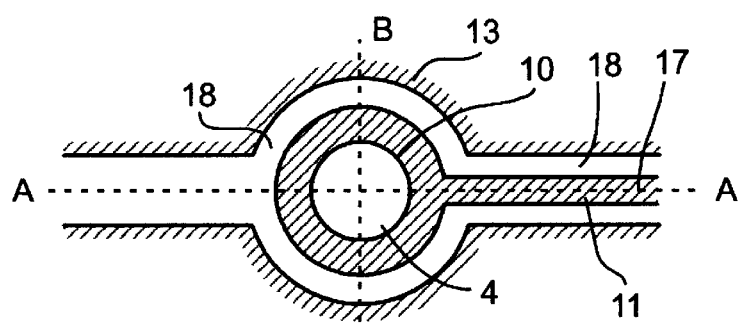

As shown in FIG. 6b, an insulating chamber 18 is etched into the substrate, preferably through the thickness of conducting layer 11, so as to insulate the transducer element from other portions of the substrate which may include other electrical components such as other transducer elements etched into the substrate. According to a specific embodiment, the width of insulating chamber 18 is about 100 $\mu$m. As shown, insulating chamber 18 is etched into the substrate so as to form a wall 10 of a predetermined thickness enclosing cavity 4, and a conducting line 17 integrally made with wall 10 for connecting the transducer element to another electronic component preferably etched into the same substrate, or to an external electronic circuit.

Figure 5A:
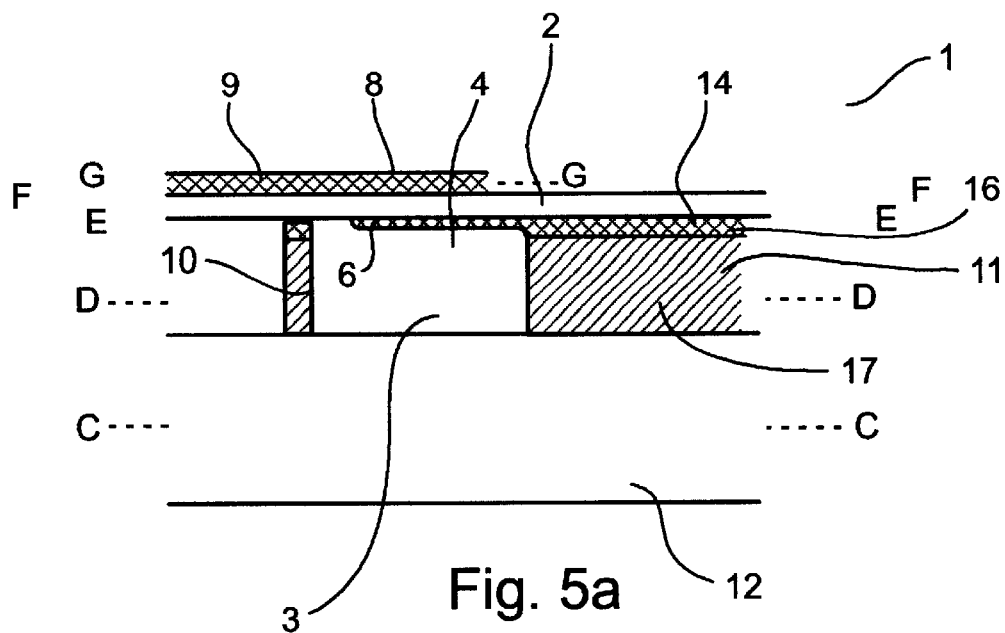
FIG. 5a is a longitudinal section of a transducer element according to the present invention taken along lines A—A in FIGS. 6a–6e.
Figure 5B:
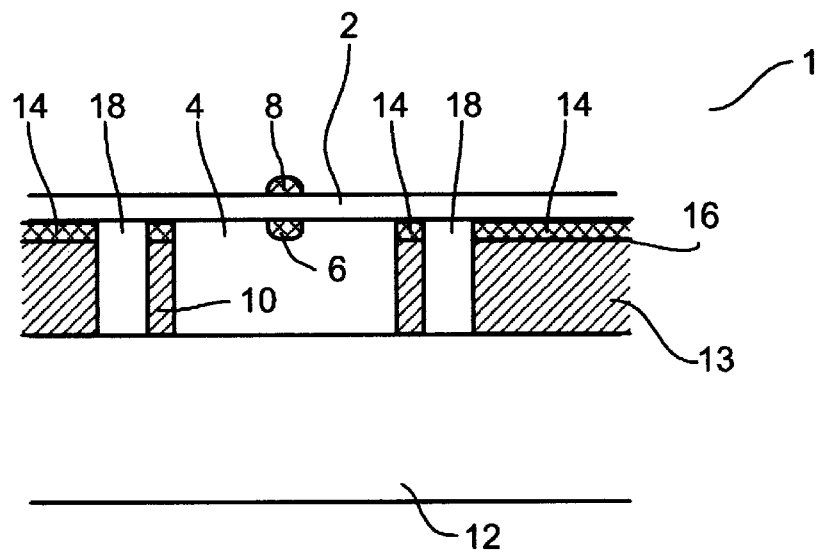
FIG. 5b is a longitudinal section of a transducer element according to the present invention taken along lines B—B in FIGS. 6a–6e.
Figure 6C:
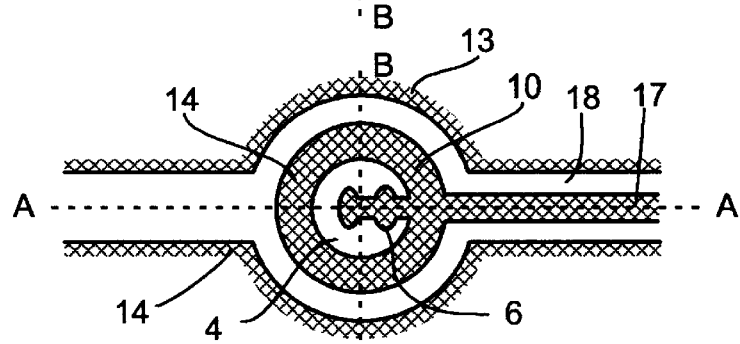
Figure 6D:
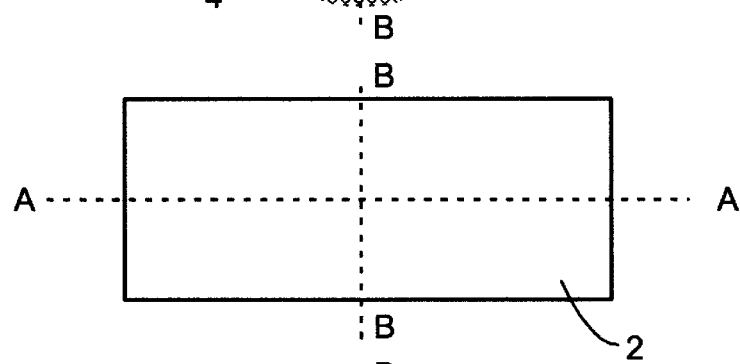
Figure 6E:
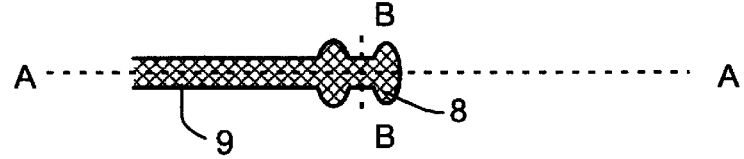

As shown in FIGS. 5a and 5b, attached to piezoelectric layer 2 are upper electrode 8 and lower electrode 6. As shown in FIGS. 6c and 6e, upper electrode 8 and lower electrode 6 are preferably precisely shaped, so as to cover a predetermined area of piezoelectric layer 2. Electrodes 6 and 8 may be deposited on the upper and lower surfaces of piezoelectric membrane 2, respectively, by using various methods such as vacuum deposition, mask etching, painting, and the like.

As shown in FIG. 5a, lower electrode 6 is preferably made as an integral part of a substantially thin electrically conducting layer 14 disposed on electrically conducting layer 11. Preferably, electrically conducting layer 14 is made of a Nickel-Copper alloy and is attached to electrically conducting layer 11 by means of a sealing connection 16. Sealing connection 16 may be made of indium. According to a preferred configuration, sealing connection 16 may feature a thickness of about 10 $\mu$m, such that the overall height of wall 10 of cavity 4 is about 20–25 $\mu$m.

As shown in FIG. 6c, electrically conducting layer 14 covers the various portions of conducting layer 11, including wall 10 and conducting line 17. The portion of conducting layer 14 covering conducting line 17 is for connection to an electronic component, as further detailed hereinunder.

According to a preferred embodiment, electrodes 6 and 8 are specifically shaped to include the most energy-productive region of piezoelectric layer 2, so as to provide maximal response of the transducer while optimizing the electrode area, and therefore the cell capacitance, thereby maximizing a selected parameter such as voltage sensitivity, current sensitivity, or power sensitivity of the transducer element.

The vertical displacement of piezoelectric layer 2, $\Psi$, resulting from a monochromatic excitation at angular frequency is modeled using the standard equation for thin plates:

$$(\nabla^2 - \gamma^2)(\nabla^2 + \gamma^2)\Psi - \frac{3(1-v^2)}{2Qh^3}P + \frac{3iZ\omega(1-v^2)}{2Qh^3}\Psi = 0$$

wherein Q is the Young's modulus representing the elasticity of layer 2; h the half-thickness of layer 2; v is the Poisson ratio for layer 2; $\gamma$ is the effective wavenumber in the layer given by: $\gamma^4 = 3\rho(1-v^2)\omega^2/Qh^2$, wherein $\rho$ is the density of layer 2 and $\omega$ is the angular frequency of the applied pressure (wherein the applied pressure may include the acoustic pressure, the static pressure differential across layer 2 and any other pressure the transducer comes across); Z is the mechanical impedance resulting from the coupling of layer 2 to both external and internal media of cavity 4, wherein the internal medium is preferably air and the external medium is preferably fluid; P is the acoustic pressure applied to layer 2, and $\overline{\Psi}$ represents the average vertical displacement of layer 2.

When chamber 4 is circular, the solution (given for a single frequency component $\omega$) representing the dynamic displacement of a circular layer 2 having a predetermined radius a, expressed in polar coordinates, is:

$$\Psi(r, \varphi) = \frac{I_1(\gamma a)[J_0(\gamma r) - J_0(\gamma a)] + J_1(\gamma a)[I_0(\gamma r) - I_0(\gamma a)]}{2h\rho\omega^2 L_0(\gamma a) + i\omega Z L_2(\gamma a)} P$$

$$L_0(z) = I_0(z)J_1(z) + J_0(z)I_1(z), \quad L_2(z) = J_2(z)I_1(z) - I_2(z)J_1(z)$$

$$Z = \frac{P_A}{i\omega H_A} + i\left[\frac{4}{3\pi} + \frac{1}{6}\right]\omega\rho_w a$$

wherein $\Psi(r,\phi)$ is time-dependent and represents the displacement of a selected point located on circular layer 2, the specific location of which is given by radius r and angle $\phi$; J and I are the normal and modified Bessel functions of the first kind, respectively; $P_A$, $H_A$ are the air pressure within cavity 4 and the height of chamber 4, respectively; and $\rho_W$ is the density of the fluid external to cavity 4.

The first term of the impedance Z relates to the stiffness resulting from compression of air within cavity 4, and the second term of Z relates to the mass added by the fluid boundary layer. An additional term of the impedance Z relating to the radiated acoustic energy is substantially negligible in this example.

The charge collected between electrodes 6 and 8 per unit area is obtained by evaluating the strains in layer 2 resulting from the displacements, and multiplying by the pertinent off-diagonal elements of the piezoelectric strain coefficient tensor, $e_{31}$, $e_{32}$, as follows:

$$Q(r, \varphi, t) = e_{31}\left(\frac{\partial \Psi}{\partial x}\right)^2 + e_{32}\left(\frac{\partial \Psi}{\partial y}\right)^2$$

wherein $Q(r,\phi,t)$ represents the charge density at a selected point located on circular layer 2, the specific location of which is given by radius r and angle $\phi$; x is the stretch direction of piezoelectric layer 2; y is the transverse direction (the direction perpendicular to the stretch direction) of layer 2; $e_{31}$, $e_{32}$ are off-diagonal elements of the piezoelectric strain coefficient tensor representing the charge accumulated at a selected point on layer 2 due to a given strain along the x and y directions, respectively, which coefficients being substantially dissimilar when using a PVDF layer. $\Psi$ is the displacement of layer 2, taken as the sum of the displacement for a given acoustic pressure P at frequency $f$, and the static displacement resulting from the pressure differential between the interior and exterior of cavity 4, which displacements being extractable from the equations given above.

The total charge accumulated between electrodes 6 and 8 is obtained by integrating $Q(r,\phi, t)$ over the entire area S of the electrode:

$$Q = \int_S Q(r, \varphi, t) d\vec{x}$$

The capacitance C of piezoelectric layer 2 is given by:

$$C = \frac{\varepsilon}{2h} \int_S d\vec{x},$$

wherein $\varepsilon$ is the dielectric constant of piezoelectric layer 2; and $2h$ is the thickness of piezoelectric layer 2.

Accordingly, the voltage, current and power responses of piezoelectric layer 2 are evaluated as follows:

$$V = \frac{2h \int_S Q(r, \varphi, t) d\vec{x}}{\varepsilon \int_S d\vec{x}}, \quad I = 2i\omega \int_S Q(r, \varphi, t) d\vec{x},$$

$$W = \frac{4ih \left[ \int_S Q(r, \varphi, t) d\vec{x} \right]^2}{\varepsilon \int_S d\vec{x}}$$

The DC components of Q are usually removed prior to the evaluation, since the DC currents are usually filtered out. The values of Q given above represent peak values of the AC components of Q, and should be modified accordingly, so as to obtain other required values such as RMS values.

According to the above, the electrical output of the transducer expressed in terms of voltage, current and power responses depend on the AC components of Q, and on the shape S of the electrodes. Further, as can be seen from the above equations, the voltage response of the transducer may be substantially maximized by minimizing the area of the electrode. The current response, however, may be substantially maximized by maximizing the area of the electrode.

Figure 7:
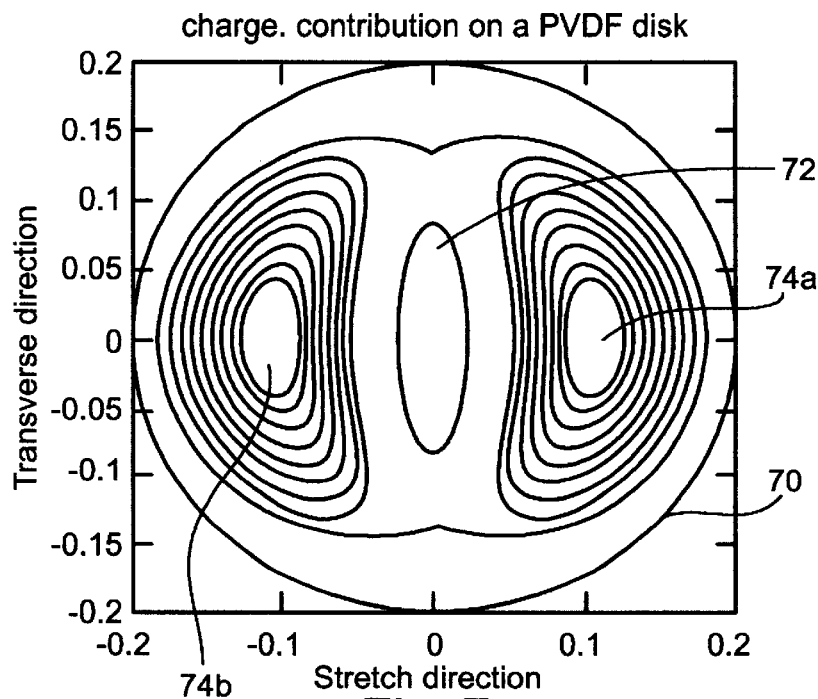
FIG. 7 shows the distribution of charge density across a piezoelectric layer of a transducer element resulting from the application of a constant pressure over the entire surface of the layer.
Figure 8A:
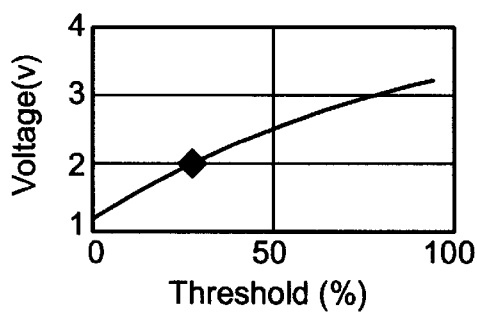
FIG. 8 shows the results of optimization performed for the power response of a transducer according to the present invention.
Figure 8C:
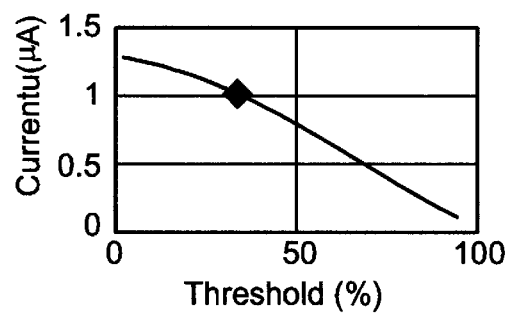
Figure 8B:
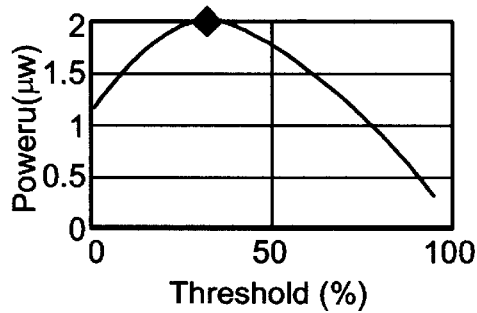
Figure 8D:
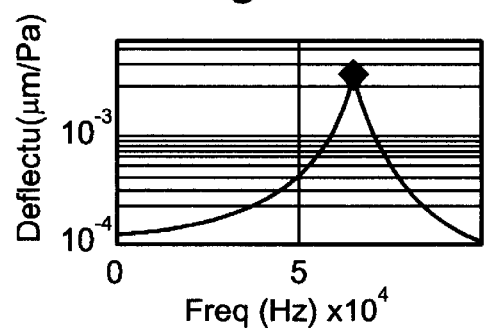

FIG. 7 shows the distribution of charge density on a circular piezoelectric layer 2 obtained as a result of pressure (acoustic and hydrostatic) applied uniformly over the entire area of layer 2, wherein specific locations on layer 2 are herein defined by using Cartesian coordinates including the stretch direction (x direction) and the transverse direction (y direction) of layer 2. It can be seen that distinct locations on layer 2 contribute differently to the charge density. The charge density vanishes at the external periphery 70 and at the center 72 of layer 2 due to minimal deformation of these portions. The charge density is maximal at two cores 74a and 74b located symmetrically on each side of center 72 due to maximal strains (in the stretch direction) of these portions.

A preferred strategy for optimizing the electrical responses of the transducer is to shape the electrode by selecting the areas contributing at least a selected threshold percentage of the maximal charge density, wherein the threshold value is the parameter to be optimized. A threshold value of 0% relates to an electrode covering the entire area of layer 2.

FIG. 8 shows the results of an optimization performed for the power response of a transducer having a layer 2 of a predetermined area. As shown in the Figure, the threshold value which provides an optimal power response is about 30% (graph b). Accordingly, an electrode which covers only the portions of layer 2 contributing at least 30% of the maximal charge density yields a maximal power response. The pertinent voltage response obtained by such an electrode is higher by a factor of 2 relative to an electrode completely covering layer 2 (graph a). The current response obtained by such electrode is slightly lower relative to an electrode completely covering layer 2 (graph c). Further, as shown in the Figure, the deflection of layer 2 is maximal when applying an acoustic signal at the resonant frequency of layer 2 (graph d).

Figure 9:
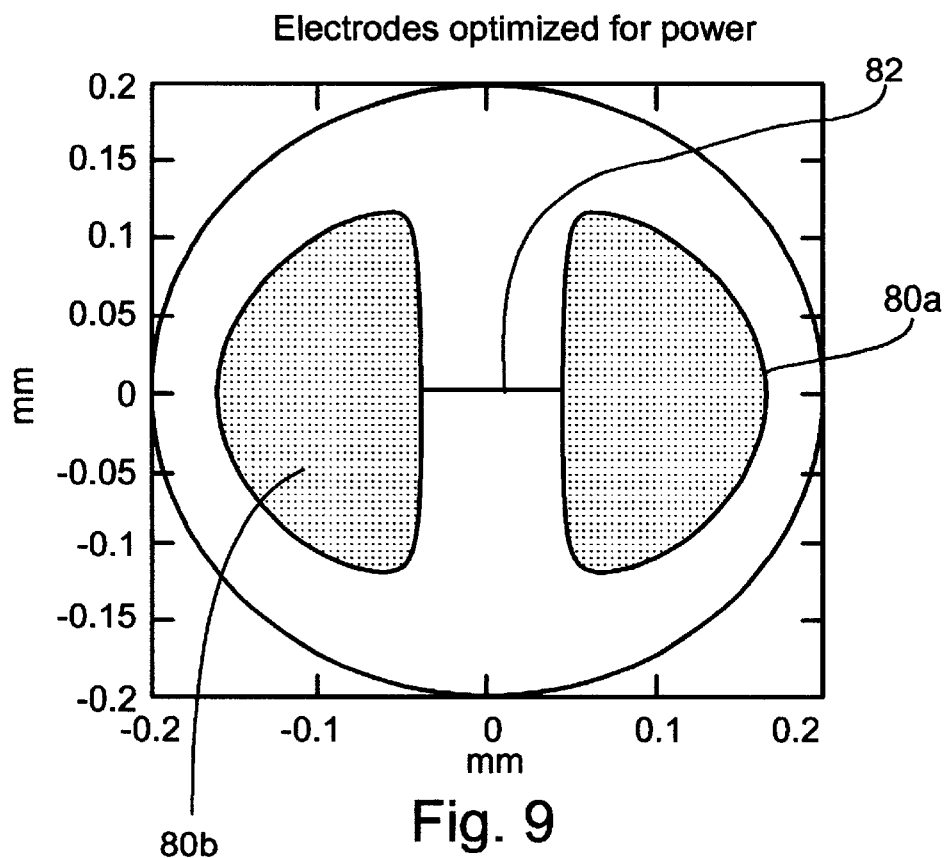
FIG. 9 shows a preferred electrode shape for maximizing the power response of a transducer according to the present invention.

A preferred electrode shape for maximizing the power response of the transducer is shown in FIG. 9, wherein the electrode includes two electrode portions 80a and 80b substantially covering the maximal charge density portions of layer 2, the electrode portions being interconnected by means of a connecting member 82 having a minimal area. Preferably, portions 80a and 80b cover the portions of layer 2 which yield at least a selected threshold (e.g. 30%) of the maximal charge density.

According to the present invention any other parameter may be optimized so as to determine the shape of electrodes 6 and 8. According to further features of the invention described in U.S. patent application Ser. No. 09/000,553, only one electrode (upper electrode 8 or lower electrode 6) may be shaped so as to provide maximal electrical response of the transducer, with the other electrode covering the entire area of layer 2. Since the charge is collected only at the portions of layer 2 received between upper electrode 8 and lower electrode 6, such configuration is operatively equivalent to a configuration including two shaped electrodes having identical shapes.

Figure 10:
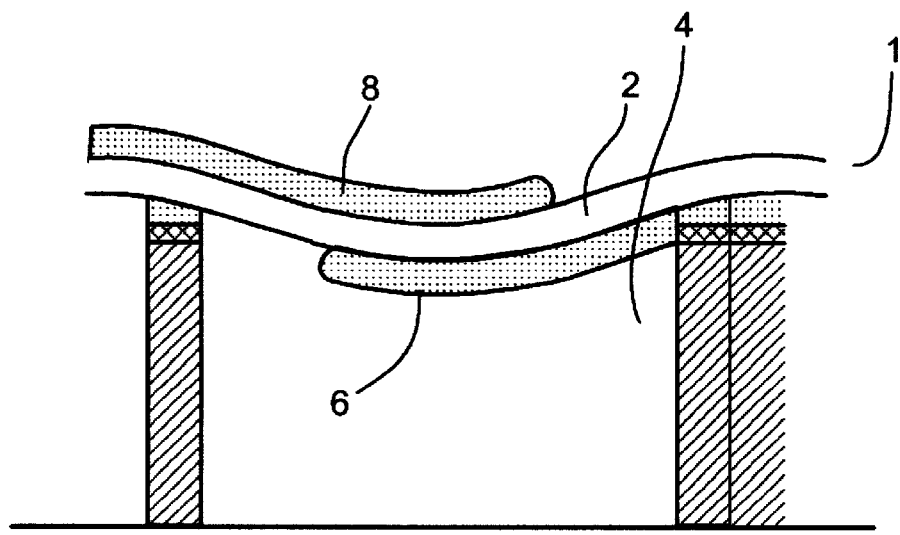
FIG. 10 is a longitudinal section of another embodiment of a transducer element according to the present invention capable of functioning as a transmitter.

Referring now to FIG. 10, according to another embodiment chamber 4 of transducer element 1 may contain gas of substantially low pressure, thereby conferring a substantially concave shape to piezoelectric membrane 2 at equilibrium. Such configuration enables to further increase the electrical response of the transducer by increasing the total charge obtained for a given displacement of layer 2. The total displacement in such an embodiment is given by: $\Psi = P_0 \Psi_{DC} + P\Psi_{AC}\cos\omega t$, wherein $P_0$ is the static pressure differential between the exterior and the interior of cavity 4; $\Psi_{DC}$ is the displacement resulting from $P_0$; P is the amplitude of the acoustic pressure; and $\Psi_{AC}$ is the displacement resulting from P.

Accordingly, the strain along the x direction includes three terms as follows:

$$S_{xx} = \left( \frac{\partial \Psi}{\partial x} \right)^2 = P_0^2 \left( \frac{\partial \Psi_{DC}}{\partial x} \right)^2 + P^2 \left( \frac{\partial \Psi_{AC}}{\partial x} \right)^2 \cos^2 \omega t + 2 P_0 P \frac{\partial \Psi_{DC}}{\partial x} \frac{\partial \Psi_{AC}}{\partial x} \cos \omega t$$

wherein the DC component is usually filtered out.

Thus, by decreasing the pressure of the medium (preferably air) within cavity 4 relative to the pressure of the external medium (preferably fluid), the value of $P_0$ is increased, thereby increasing the value of the third term of the above equation.

Such embodiment makes it possible to increase the charge output of layer 2 for a given displacement, thereby increasing the voltage, current and power responses of the transducer without having to increase the acoustic pressure P. Furthermore, such embodiment enables to further miniaturize the transducer since the same electrical response may be obtained for smaller acoustic deflections. Such embodiment is substantially more robust mechanically and therefore more durable than the embodiment shown in FIGS. 5a and 5b. Such further miniaturization of the transducer enables to use higher resonance frequencies relative to the embodiment shown in FIGS. 5a and 5b.

Preferably, a transducer element 1 according to the invention described in U.S. patent application Ser. No. 09/000,553 is fabricated by using technologies which are in wide use in the microelectronics industry, so as to allow integration thereof with other conventional electronic components as further detailed hereinunder. When the transducer element includes a substrate such as Copper-polymer laminate or silicon, a variety of conventional electronic components may be fabricated onto the same substrate.

According to a preferred embodiment, a plurality of cavities 4 may be etched into a single substrate 12 and covered by a single piezoelectric layer 2, so as to provide a transducer element including a matrix of transducing cell members 3, thereby providing a larger energy collecting area of predetermined dimensions, while still retaining the advantage of miniature individual transducing cell members 3. When using such configuration, the transducing cell members 3 may be electrically interconnected in parallel or serial connections, or combinations thereof, so as to tailor the voltage and current response of the transducer. Parallel connections are preferably used so as to increase the current output while serial connections are preferably used so as to increase the voltage output of the transducer.

Furthermore, piezoelectric layer 2 may be completely depolarized and then repolarized at specific regions thereof, so as to provide a predetermined polarity to each of the transducing cell members 3. Such configuration enables to reduce the complexity of interconnections between cell members 3.

A transducer element according to the invention described in U.S. patent application Ser. No. 09/000,553 may be further used as a transmitter for transmitting information to a remote receiver by modulating the reflection of an external impinging acoustic wave arrived from a remote transmitter.

Referring to FIG. 10, the transducer element shown may function as a transmitter element due to the asymmetric fluctuations of piezoelectric layer 2 with respect to positive and negative transient acoustic pressures obtained as a result of the pressure differential between the interior and exterior of cavity 4.

A transmitter element according to the present invention preferably modulates the reflection of an external impinging acoustic wave by means of a switching element connected thereto. The switching element encodes the information that is to be transmitted, such as the output of a sensor, thereby frequency modulating a reflected acoustic wave.

Such configuration requires very little expenditure of energy from the transmitting module itself, since the acoustic wave that is received is externally generated, such that the only energy required for transmission is the energy of modulation.

Specifically, the reflected acoustic signal is modulated by switching the switching element according to the frequency of a message electric signal arriving from another electronic component such as a sensor, so as to controllably change the mechanical impedance of layer 2 according to the frequency of the message signal.

Preferably, a specific array of electrodes connected to a single cell member or alternatively to a plurality of cell members are used, so as to control the mechanical impedance of layer 2.

Figure 11D:
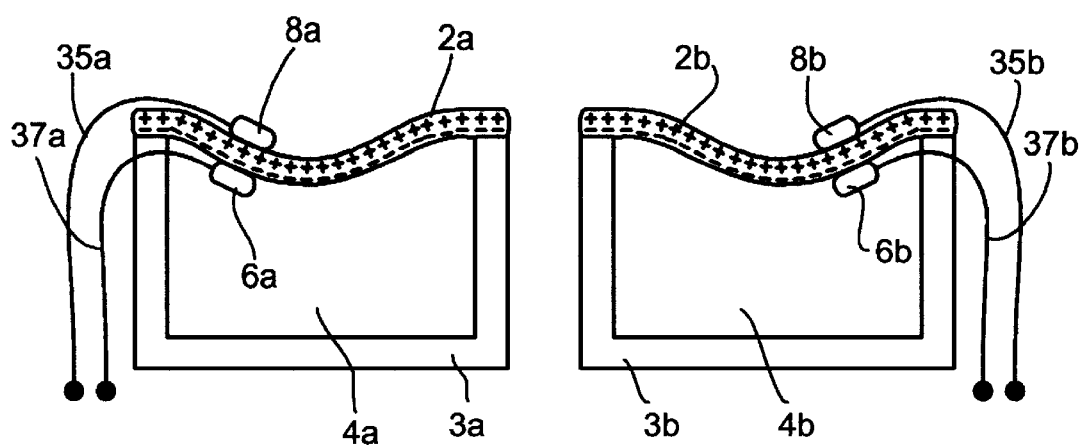

FIGS. 11a–11g illustrate possible configurations for controllably change the impedance of layer 2 of a transmitter element. Referring to FIG. 11a, a transmitter element according to the invention described in U.S. patent application Ser. No. 09/000,553 may include a first and second pairs of electrodes, the first pair including an upper electrode 40a and a lower electrode 38a, and the second pair including an upper electrode 40b and a lower electrode 38b. Electrodes 38a, 38b, 40a and 40b are electrically connected to an electrical circuit by means of conducting lines 36a, 36b, 34a and 34b, respectively, the electrical circuit including a switching element (not shown), so as to alternately change the electrical connections of conducting lines 36a, 36b, 34a and 34b.

Preferably, the switching element switches between a parallel connection and an anti-parallel connection of the electrodes. A parallel connection decreases the mechanical impedance of layer 2, wherein an anti-parallel connection increases the mechanical impedance of layer 2. An anti-parallel connection may be obtained by interconnecting line 34a to 36b and line 34b to 36a. A parallel connection may be obtained by connecting line 34a to 34b and line 36a to 36b. Preferably, the switching frequency equals the frequency of a message signal arriving from an electrical component such as a sensor as further detailed hereinunder.

According to another embodiment shown in FIG. 11b, upper electrode 40a is connected to lower electrode 38b by means of a conducting line 28, and electrodes 38a and 40b are connected to an electrical circuit by means of connecting lines 27 and 29, respectively, wherein the electrical circuit further includes a switching element. Such configuration provides an anti-parallel connection of the electrodes, wherein the switching element functions as an on/off switch, thereby alternately increasing the mechanical impedance of layer 2.

In order to reduce the complexity of the electrical connections, layer 2 may be depolarized and then repolarized at specific regions thereof. As shown in FIG. 11c, the polarity of the portion of layer 2 received between electrodes 40a and 38a is opposite to the polarity of the portion of layer 2 received between electrodes 40b and 38b. An anti-parallel connection is thus achieved by interconnecting electrodes 38a and 38b by means of a conducting line 28, and providing conducting lines 27 and 29 connected to electrodes 40a and 40b, respectively, the conducting lines for connection to an electrical circuit including a switching element.

According to another embodiment, the transmitting element includes a plurality of transducing cell members, such that the mechanical impedance of layer 2 controllably changed by appropriately interconnecting the cell members.

As shown in FIG. 11d, a first transducing cell member 3a including a layer 2a and a cavity 4a, and a second transducing cell member 3b including a layer 2b and a cavity 4b are preferably contained within the same substrate; and layers 2a and 2b are preferably integrally made. A first pair of electrodes including electrodes 6a and 8a is attached to layer 2, and a second pair of electrode including electrodes 6b and 8b is attached to layer 2b. Electrodes 6a, 8a, 6b and 8b are electrically connected to an electrical circuit by means of conducting lines 37a, 35a, 37b and 35b, respectively, the electrical circuit including a switching element, so as to alternately switch the electrical connections of conducting lines 37a, 35a, 37b and 35b, so as to alternately provide parallel and anti-parallel connections, substantially as described for FIG. 11a, thereby alternately decreasing and increasing the mechanical impedance of layers 2a and 2b.

Figure 11E:
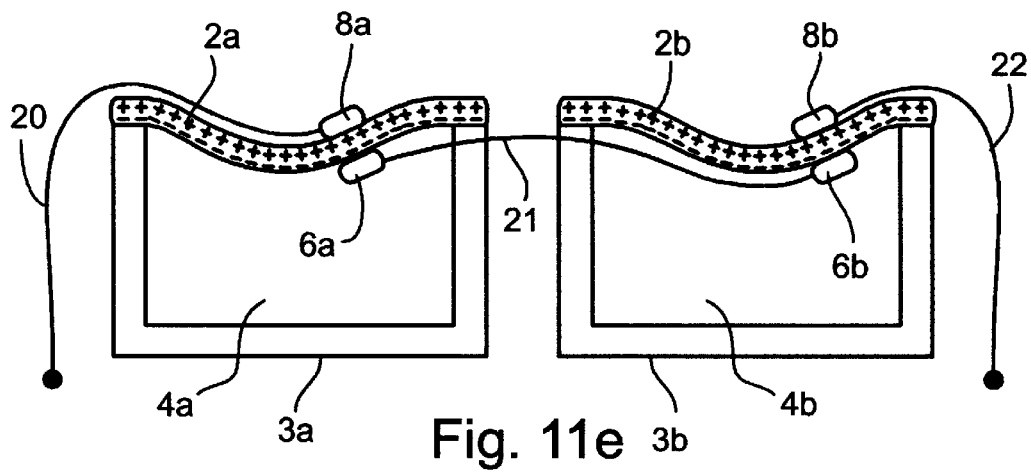

FIG. 11e illustrates another embodiment, wherein the first and second transducing cell members are interconnected by means of an anti-parallel connection. As shown in the Figure, the polarity of layer 2a is opposite to the polarity of layer 2b, so as to reduce the complexity of the electrical connections between cell members 3a and 3b. Thus, electrode 6a is connected to electrode 6b by means of a conducting line 21, and electrodes 8a and 8b are provided with conducting lines 20 and 22, respectively, for connection to an electrical circuit which includes a switching element, wherein the switching element preferably functions as an on/off switch, so as to alternately increase the mechanical impedance of layers 2a and 2b.

Figure 11F:
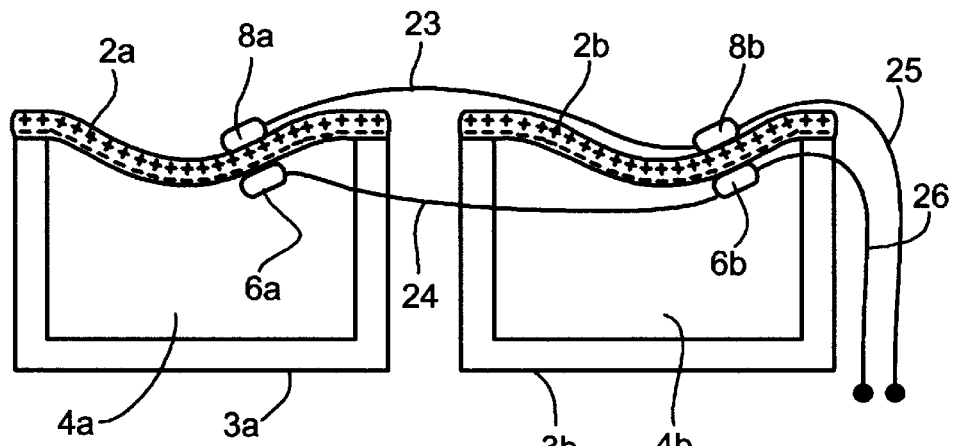

FIG. 11f shows another embodiment, wherein the first and second transducing cell members are interconnected by means of a parallel connection. As shown, electrodes 6a and 6b are interconnected by means of conducting line 24, electrodes 8a and 8b are interconnected by means of conducting line 23, and electrodes 6b and 8b are provided with conducting lines 26 and 25, respectively, the conducting lines for connection to an electrical circuit including a switching element. The switching element preferably functions as an on/off switch for alternately decreasing and increasing the mechanical impedance of layers 2a and 2b.

Figure 12:
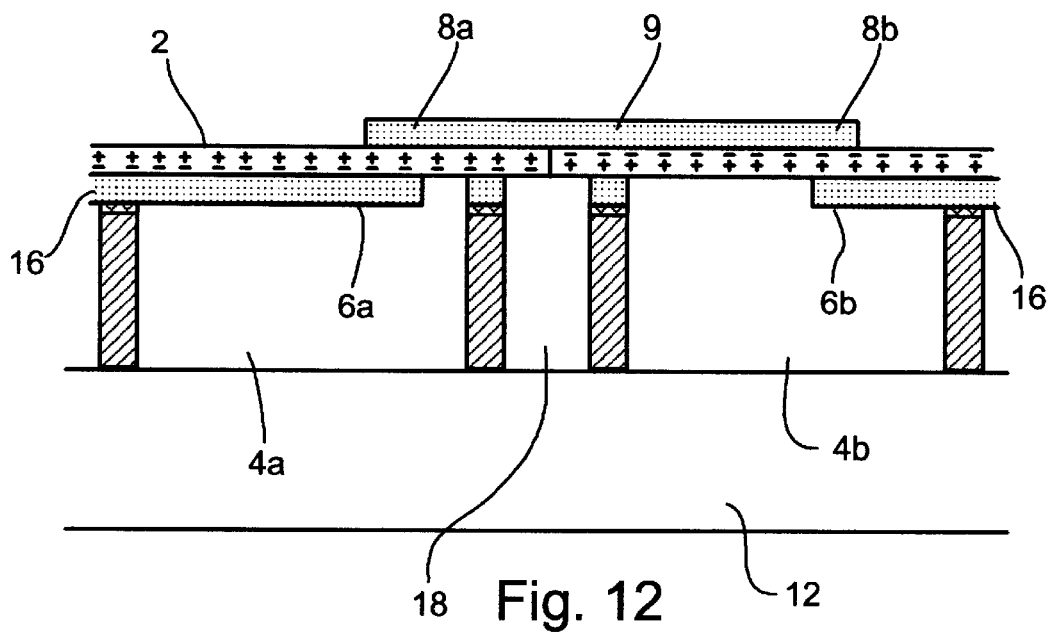
FIG. 12 is a longitudinal section of a transmitter element according to the present invention including an anti-parallel electrical connection.

FIG. 12 shows a possible configuration of two transducing cell members etched onto the same substrate and interconnected by means of an anti-parallel connection. As shown in the Figure, the transducing cell members are covered by a common piezoelectric layer 2, wherein the polarity of the portion of layer 2 received between electrodes 6a and 8a is opposite to the polarity of the portion of layer 2 received between electrodes 6b and 8b. Electrodes 8a and 8b are bonded by means of a conducting line 9, and electrodes 6a and 6b are provided with conducting lines 16 for connection to an electrical circuit.

Figure 13:
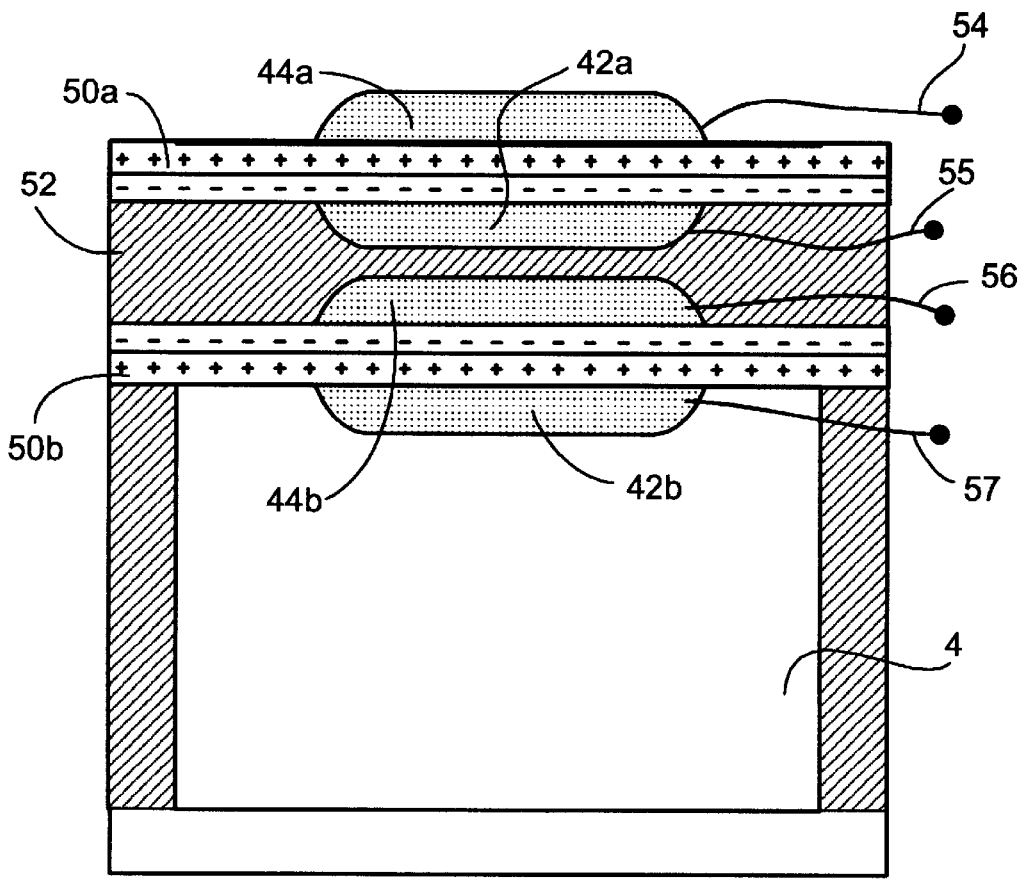
FIG. 13 is a longitudinal section of another embodiment of a transmitter element according to the present invention.

Another embodiment of a transmitter element according to the present invention is shown in FIG. 13. The transmitter element includes a transducing cell member having a cavity 4 covered by a first and second piezoelectric layers, 50a and 50b, preferably having opposite polarities. Preferably, layers 50a and 50b are interconnected by means of an insulating layer 52. Attached to layer 50a are upper and lower electrodes 44a and 42a, and attached to layer 50b are upper and lower electrodes 44b and 42b. Electrodes 44a, 42a, 44b and 42b are provided with conducting lines 54, 55, 56 and 57, respectively, for connection to an electrical circuit.

It will be appreciated that the above descriptions are intended only to serve as examples, and that many other embodiments are possible within the spirit and the scope of invention described in U.S. patent application Ser. No. 09/000,553.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A telemetry system for providing spatial positioning information from within a patient's body, the system comprising at least one implantable telemetry unit including:
   (a) at least one first transducer being for converting a power signal received from outside the body, into electrical power for powering said at least one implantable telemetry unit;
   (b) at least one second transducer being for receiving a positioning field signal being received from outside the body; and
   (c) at least one third transducer being for transmitting a locating signal transmittable outside the body in response to said positioning field signal.

2. The telemetry system of claim 1, wherein said power signal is selected from the group consisting of a radio frequency signal, an acoustic signal and a magnetic field signal.

3. The telemetry system of claim 1, wherein said positioning field signal is selected from the group consisting of a radio frequency signal, an acoustic signal and a magnetic field signal.

4. The telemetry system of claim 1, wherein said locating signal is selected from the group consisting of a radio frequency signal, an acoustic signal and a magnetic field signal.

5. The telemetry system of claim 1, wherein said at least one implantable telemetry unit further includes a processor, said processor being in communication with said at least one first said at least one second and said at least one third transducers, said processor being for receiving a first electrical signal converted by said at least one second transducer from said positioning field signal and for returning a processed second electrical signal to said at least one third transducer, such that said second electrical signal is converted into said locating signal by said at least one third transducer.

6. The telemetry system of claim 1, wherein said at least one first transducer and said at least one third transducer are a single transducer.

7. The telemetry system of claim 6, wherein said single transducer is selected from the group consisting of radio frequency transducer, an acoustic transducer and a magnetic field transducer.

8. The telemetry system of claim 1, wherein each of said at least one implantable telemetry unit has an identification code associated therewith.

9. The telemetry system of claim 8, wherein information pertaining to said identification code is included within said locating signal.

10. The telemetry system of claim 9, wherein said at least one implantable telemetry unit is implanted in a specific predefined region of a patient's body and further wherein said identification code includes predefined spatial positioning information.

11. The telemetry system of claim 1, further comprising an extracorporeal unit including:
   (c) generating unit for generating said power signal and said positioning field signal;
   (d) at least one fourth transducer being coupled to said generating unit for transmitting said power signal to said at least one implantable telemetry unit;
   (e) at least one fifth transducer being coupled to said generating unit, said at least one fifth transducer being for transmitting said positioning field signal receivable by said at least one implantable telemetry unit; and
   (f) at least one sixth transducer being coupled to said generating unit, said at least one sixth transducer being for receiving said locating signal transmitted from said at least one implantable telemetry unit.

12. The telemetry system of claim 11, wherein said at least one fourth, at least one fifth and said at least one sixth transducers are each independently selected form the group consisting of a radio frequency transducer, an acoustic transducer and a magnetic field transducer.

13. The telemetry system of claim 11, wherein said at least one fourth transducer and said at least one sixth transducer are a single transducer.

14. The telemetry system of claim 13, wherein said single transducer is selected from the group consisting of a radio frequency transducer, an acoustic transducer and a magnetic field transducer.

15. The telemetry system of claim 13, wherein said extracorporeal unit is integratable into a medical instrument.

16. The telemetry system of claim 1, wherein said at least one first, said at least one second and said at least one third transducers are each independently selected form the group consisting of a radio frequency transducer, an acoustic transducer and a magnetic field transducer.

17. The telemetry system of claim 16, wherein said at least one first transducer and said at least one third transducer are each independently an acoustic transducer which-includes:
 (i) a cell member having a cavity;
 (ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and
 (iii) a first electrode attached to said external surface and a second electrode attached to said internal surface.

18. The telemetry system of claim 17, wherein said piezoelectric layer is of a material selected from the group consisting of PVDF and piezoceramic.

19. The telemetry system of claim 16, wherein said magnetic field transducer is selected from the group consisting of multiturn wire coils, coils implemented in a very large scale integration (VLSI) silicon devices, a Hall effect detector, a coupled split-drain field effect transistor (MAGFET) device, and a magnetoresistive field effect transistor (FET) detector.

20. The telemetry system of claim 16, wherein said magnetic field transducer of said at least one first transducer includes at least one coil for converting a magnetic field signal into an electrical current.

21. The telemetry system of claim 16, wherein said magnetic field transducer of said at least one second or third transducer includes a plurality of transducers, each serves for converting a magnetic field signal into an electrical signal.

22. The telemetry system of claim 21, wherein said plurality of transducers are oriented in three mutually orthogonal planes.

23. A method for obtaining spatial positioning information from within a patient's body, the method comprising the steps of:
 (a) implanting within the patient's body at least one telemetry unit including:
  (i) at least one first transducer being for converting a power signal received from outside the body, into electrical power for powering said at least one implantable telemetry unit;
  (ii) at least one second transducer being for receiving a positioning field signal being received from outside the body; and
  (iii) at least one third transducer being for transmitting a locating signal transmittable outside the body in response to said positioning field signal; and
 (b) receiving said locating signal outside the body of the patient, such that said location of said at least one telemetry unit within the body of the patient is identified from said locating signal.

24. The method of claim 23, wherein the spatial positioning information is used to direct radiation to a specific region within the patient's body.

25. The method of claim 23, wherein said power signal is selected from the group consisting of a radio frequency signal, an acoustic signal and a magnetic field signal.

26. The method of claim 23, wherein said positioning field signal is selected from the group consisting of a radio frequency signal, an acoustic signal and a magnetic field signal.

27. The method of claim 23, further comprising the step of processing a first electrical signal converted by said at least one second transducer from said positioning field signal and returning a processed second electrical signal to said at least one third transducer via a processor being within said at least one telemetry unit, such that said second electrical signal is converted into said locating signal by said at least one third transducer.

28. The method of claim 23, wherein said radiation is selected from the group consisting of ultrasonic radiation and ionizing radiation.

29. The method of claim 28, wherein said ionizing radiation is selected from the group consisting of alpha radiation, beta radiation, gamma radiation, X-ray radiation and neutron radiation.

30. The method of claim 23, wherein said at least one first transducer and said at least one third transducer are a single transducer.

31. The method of claim 30, wherein said single transducer is selected from the group consisting of radio frequency transducer, an acoustic transducer and a magnetic field transducer.

32. The method of claim 23, wherein the step of receiving said locating signal outside the body of the patient is further effected by an extracorporeal monitoring unit telemetrically communicating with said at least one telemetry unit.

33. The method of claim 32, wherein the step of telemetrically communicating is achieved via a signal selected from the group consisting of an acoustic signal, a magnetic signal and a radio frequency signal.

34. The method of claim 23, wherein each of said at least one telemetry unit has an identification code associated therewith.

35. The method of claim 34, wherein information pertaining to said identification code is included within said locating signal.

36. The method of claim 34, wherein said at least one telemetry unit is implanted in a specific predefined region of the patient's body and further wherein said identification code includes predefined spatial positioning information.

37. The method of claim 23, wherein said at least one first and said at least one third transducers are each independently selected from the group consisting of a radio frequency transducer, an acoustic transducer and a magnetic field transducer.

38. The method of claim 37, wherein said at least one first transducer and said at least one third transducer are each independently an acoustic transducer which-includes:
 (i) a cell member having a cavity;
 (ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and
 (iii) a first electrode attached to said external surface and a second electrode attached to said internal surface.

39. The method of claim 38, wherein said piezoelectric layer is of a material selected from the group consisting of PVDF and piezoceramic.

40. The method of claim 37, wherein said magnetic field transducer is selected from the group consisting of multiturn wire coils, coils implemented in a very large scale integration (VLSI) silicon devices, a Hall effect detector, a coupled split-drain field effect transistor (MAGFET) device, and a magnetoresistive field effect transistor (FET) detector.

41. The method of claim 37, wherein said magnetic field transducer of said at least one first transducer includes at least one coil for converting a magnetic field signal into an electrical current.

42. The method of claim 37, wherein said magnetic field transducer of said at least one second transducer includes a plurality of transducers each for converting a magnetic field signal into an electrical signal.

43. The method of claim 42, wherein said plurality of transducers are oriented in three mutually orthogonal planes.

* * * * *